(12) United States Patent
Wei et al.

(10) Patent No.: US 11,045,649 B2
(45) Date of Patent: Jun. 29, 2021

(54) INCONTINENCE THERAPY

(71) Applicant: Medtronic, Inc., Minneapolis, MN (US)

(72) Inventors: Xuan K. Wei, Minnetonka, MN (US); Ryan D. Willemsen, St. Paul, MN (US); Dwight E. Nelson, Shoreview, MN (US); Sudha B. Iyer, St. Paul, MN (US); Kira Stolen, St. Paul, MN (US); Xin Su, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 601 days.

(21) Appl. No.: 15/436,287

(22) Filed: Feb. 17, 2017

(65) Prior Publication Data
US 2017/0239470 A1    Aug. 24, 2017

Related U.S. Application Data

(60) Provisional application No. 62/297,554, filed on Feb. 19, 2016.

(51) Int. Cl.
*A61N 1/36* (2006.01)
*A61N 1/372* (2006.01)
*A61N 1/05* (2006.01)

(52) U.S. Cl.
CPC ....... *A61N 1/36007* (2013.01); *A61N 1/0514* (2013.01); *A61N 1/36135* (2013.01);
(Continued)

(58) Field of Classification Search
CPC .............. A61N 1/0514; A61N 1/36007; A61N 1/36031; A61N 1/3606; A61N 1/36128;
(Continued)

(56) References Cited

U.S. PATENT DOCUMENTS

| 4,607,639 A | 8/1986 | Tanagho et al. |
| 4,739,764 A | 4/1988 | Lue et al. |

(Continued)

FOREIGN PATENT DOCUMENTS

| WO | 0154767 A1 | 8/2001 |
| WO | 2004093978 A1 | 11/2004 |

(Continued)

OTHER PUBLICATIONS

"For Sacral Neuromodulation Therapy", Clinician Programming Guide for the InterStim™ System, May 30, 2018, 60 pp.

(Continued)

*Primary Examiner* — Eugene T Wu
(74) *Attorney, Agent, or Firm* — Shumaker & Sieffert, P.A.

(57) ABSTRACT

In some examples, a technique for delivering electrical stimulation therapy to a patient includes determining, by processing circuitry, one or more cycle settings associated with delivery of the electrical stimulation therapy, determining, by the processing circuitry, a cycle time period associated with each cycle setting, and delivering, by a medical device, electrical stimulation therapy based on the determined cycle settings and the determined cycle time periods. Each cycle setting may define an on-cycle, during which electrical stimulation is delivered, and an off-cycle, during which electrical stimulation is not delivered. The technique further may include delivering electrical stimulation to the patient to provide one or more reminders to the patient, such as a reminder to void or a reminder of the existence of electrical stimulation.

37 Claims, 11 Drawing Sheets

(52) U.S. Cl.
CPC ..... *A61N 1/36164* (2013.01); *A61N 1/36175* (2013.01); *A61N 1/37247* (2013.01)

(58) Field of Classification Search
CPC ............ A61N 1/36132; A61N 1/36135; A61N 1/36139; A61N 1/3614; A61N 1/36146; A61N 1/3615; A61N 1/36153; A61N 1/36157; A61N 1/36164; A61N 1/36167; A61N 1/36175; A61N 1/37258; A61B 5/202; A61B 5/204; A61B 5/4809; A61B 5/4812; A61B 5/4848; A61B 5/74; A61B 5/7455

See application file for complete search history.

(56) References Cited

U.S. PATENT DOCUMENTS

| | | | |
|---|---|---|---|
| 5,562,717 A * | 10/1996 | Tippey | A61B 5/227 607/138 |
| 6,266,557 B1 | 7/2001 | Roe et al. | |
| 6,449,512 B1 | 9/2002 | Boveja | |
| 6,652,449 B1 | 11/2003 | Gross et al. | |
| 6,735,474 B1 | 5/2004 | Loeb et al. | |
| 6,907,293 B2 | 6/2005 | Grill et al. | |
| 6,941,171 B2 | 9/2005 | Mann et al. | |
| 6,990,376 B2 | 1/2006 | Tanagho et al. | |
| 7,047,078 B2 | 5/2006 | Boggs, II et al. | |
| 7,276,057 B2 | 10/2007 | Gerber | |
| 7,280,867 B2 | 10/2007 | Frei et al. | |
| 7,489,970 B2 | 2/2009 | Lee et al. | |
| 7,505,815 B2 | 3/2009 | Lee et al. | |
| 7,548,786 B2 | 6/2009 | Lee et al. | |
| 8,521,292 B2 | 8/2013 | Wei et al. | |
| 8,989,861 B2 | 3/2015 | Su et al. | |
| 9,089,699 B2 | 7/2015 | Su et al. | |
| 9,155,885 B2 | 10/2015 | Wei et al. | |
| 9,185,489 B2 | 11/2015 | Gerber et al. | |
| 9,409,020 B2 | 8/2016 | Parker | |
| 9,433,783 B2 | 9/2016 | Wei et al. | |
| 9,533,155 B2 | 1/2017 | Jiang et al. | |
| 9,724,509 B2 | 8/2017 | Su et al. | |
| 10,149,978 B1 | 12/2018 | Park | |
| 10,518,086 B2 | 12/2019 | Su et al. | |
| 10,576,282 B2 | 3/2020 | Doan et al. | |
| 2003/0100930 A1 | 5/2003 | Cohen et al. | |
| 2003/0135248 A1 * | 7/2003 | Stypulkowski | A61N 1/36071 607/73 |
| 2004/0199218 A1 | 10/2004 | Lee et al. | |
| 2005/0060005 A1 | 3/2005 | Boggs, II et al. | |
| 2005/0070969 A1 | 3/2005 | Gerber | |
| 2005/0143783 A1 * | 6/2005 | Boveja | A61N 1/36007 607/40 |
| 2005/0222636 A1 | 10/2005 | Grill et al. | |
| 2005/0222641 A1 * | 10/2005 | Pless | A61N 1/36064 607/45 |
| 2005/0261746 A1 | 11/2005 | Gross et al. | |
| 2006/0020297 A1 | 1/2006 | Gerber et al. | |
| 2006/0190046 A9 | 8/2006 | Gerber | |
| 2006/0190047 A1 | 8/2006 | Gerber et al. | |
| 2006/0190048 A1 | 8/2006 | Gerber | |
| 2006/0190049 A1 | 8/2006 | Gerber et al. | |
| 2006/0195152 A1 | 8/2006 | Gerber | |
| 2006/0247723 A1 | 11/2006 | Gerber et al. | |
| 2006/0259099 A1 | 11/2006 | Goetz et al. | |
| 2006/0293719 A1 | 12/2006 | Naghavi | |
| 2007/0027494 A1 | 2/2007 | Gerber | |
| 2007/0027495 A1 | 2/2007 | Gerber | |
| 2007/0100387 A1 | 5/2007 | Gerber | |
| 2007/0100388 A1 * | 5/2007 | Gerber | A61N 1/36007 607/41 |
| 2007/0293906 A1 | 12/2007 | Cowan et al. | |
| 2008/0294226 A1 | 11/2008 | Moffitt et al. | |
| 2008/0300449 A1 * | 12/2008 | Gerber | A61N 1/36007 600/30 |
| 2008/0300650 A1 | 12/2008 | Gerber et al. | |
| 2009/0036946 A1 | 2/2009 | Cohen et al. | |
| 2009/0054950 A1 | 2/2009 | Stephens | |
| 2009/0083070 A1 * | 3/2009 | Giftakis | A61N 1/36132 705/2 |
| 2009/0138061 A1 | 5/2009 | Stephens et al. | |
| 2009/0222058 A1 | 9/2009 | Craggs | |
| 2009/0306460 A1 | 12/2009 | Stephens et al. | |
| 2010/0094372 A1 | 4/2010 | Grill et al. | |
| 2012/0010680 A1 * | 1/2012 | Wei | A61N 1/36007 607/40 |
| 2013/0079841 A1 * | 3/2013 | Su | A61N 1/36007 607/41 |
| 2013/0289659 A1 * | 10/2013 | Nelson | A61N 1/36007 607/59 |
| 2016/0114167 A1 | 4/2016 | Jiang et al. | |
| 2016/0339250 A1 | 11/2016 | Kaula et al. | |
| 2016/0354028 A1 | 12/2016 | Damaser et al. | |
| 2016/0367803 A1 | 12/2016 | Wei et al. | |
| 2017/0087369 A1 * | 3/2017 | Bokil | A61N 1/37241 |
| 2017/0239470 A1 | 8/2017 | Wei et al. | |
| 2017/0291031 A1 | 10/2017 | Lee | |
| 2018/0133484 A1 | 5/2018 | Dinsmoor et al. | |
| 2019/0009098 A1 | 1/2019 | Jiang et al. | |
| 2019/0060647 A1 | 2/2019 | Su et al. | |
| 2020/0078594 A1 | 3/2020 | Jiang et al. | |

FOREIGN PATENT DOCUMENTS

| | | |
|---|---|---|
| WO | 2010123704 A2 | 10/2010 |
| WO | 2018/089418 A1 | 5/2018 |

OTHER PUBLICATIONS

"Information for Prescribers", Medtronic InterStim™ System, May 30, 2018, 22 pp.

Su et al., "Electromyographic Responses Across Different Pulse-Widths of Sacral Neuromodulation in Sheep", Neuromodulation, Feb. 20, 2018, 6 pp.

"Interstim Therapy—N'Vision® Model 8840 Clinician Programmer and Model 8870 Application Card", InterStim® Model 8870 Programming Guide for Software Version B, May 2008, 160 pp.

"Programming Pointers N'Vision® Clinician Programmer", InterStim® Therapy, 150 pp., Applicant points out, in accordance with MPEP 609.04(a), that the year of publication, 2006, is sufficiently earlier than the effective U.S. filing date, so that the particular month of publication is not in issue.

Siegel et al., "Prospective Randomized Feasibility Study Assessing the Effect of Cyclic Sacral Neuromodulation on Urinary Urge Incontinence in Women", Female Pelvic Medicine & Reconstructive Surgery, vol. 00, No. 00, Sep. 2017, 5 pp.

Amend et al. "How Does Sacral Modulation Work Best? Placement and Programming Techniques to Maximize Efficacy", Curr Urol Rep, vol. 12, Jun. 28, 2011, pp. 327-335.

Marcelissen et al., "The Effect of Pulse Rate Changes on the Clinical Outcome of Sacral Neuromodulation", The Journal of Urology, vol. 185, May 2011, pp. 1781-1785.

Beer et al., "Cycling Versus Continuous Mode in Neuromodulator Programming: A Crossover Randomized Control Trial", Urol Nurs., vol. 36 (3), May-Jun. 2016, pp. 123-132.

Hoen et al., "Intermittent Sacral Neuromodulation for Idiopathic Urgency Urinary Incontinence in Women", Neurourology and Urodynamics, vol. 36, Dec. 3, 2015, pp. 385-389.

Oerlemans et al., "Is on-Demand Sacral Neuromodulation in Patients With OAB Syndrome a Feasible Therapy Regime?", Neurourology and Urodynamics, vol. 30, Aug. 8, 2011, pp. 1493-1496.

Van Der Pal et al., "Percutaneous tibial nerve stimulation in the treatment of refractory overactive bladder syndrome: is maintenance treatment necessary?", BJU International, Mar. 2006, pp. 547-550.

Price et al., "Prospective Randomized Crossover Trial Comparing Continuous and Cyclic Stimulation in InterStim Therapy", Female Pelvic Medicine & Reconstructive Surgery, vol. 21, No. 6, Nov./Dec. 2015, pp. 355-358.

(56) References Cited

OTHER PUBLICATIONS

Cadish et al., "Stimulation Latency and Comparison of Cycling Regimens in Women Using Sacral Neuromodulation", Neurourology and Urodynamics, vol. 36, Feb. 1, 2016, pp. 486-489.

Burton et al., "Effectiveness of Percutaneous Posterior Tibial Nerve Stimulation for Overactive Bladder: A Systematic Review and Meta-Analysis", Neurourology and Urodynamics, vol. 31, May 11, 2012, pp. 1206-1216.

* cited by examiner

INCONTINENCE THERAPY

This application claims the benefit of U.S. Provisional Application Ser. No. 62/297,554, which names inventors Wei et al. and was filed on Feb. 19, 2016. U.S. Provisional Application Ser. No. 62/297,554 is incorporated herein by reference in its entirety.

TECHNICAL FIELD

The disclosure relates to medical devices and, more particularly, to medical devices configured to deliver electrical stimulation therapy.

BACKGROUND

Urinary incontinence, or an inability to control urinary function, is a problem that afflicts people of all ages, genders, and races. Various muscles, nerves, organs, and conduits within the pelvic floor cooperate to collect, store, and release urine. A variety of disorders may compromise a patient's urinary tract performance and contribute to incontinence. Many such disorders may be associated with aging, injury, or illness.

Urinary incontinence, or degree of urgency associated with incontinence, may originate from disorders of portions of the peripheral or central nervous system which control the bladder micturition reflex. Nerve disorders may also lead to overactive bladder activities and/or may prevent proper triggering and operation of the bladder. Furthermore, urinary incontinence may also result from improper communication between the nervous system and the bladder.

SUMMARY

Devices, systems, and techniques for managing incontinence (bladder incontinence and/or fecal incontinence) of a patient and/or other patient conditions using electrical stimulation are described in this disclosure. In some examples, a medical device is configured to deliver electrical stimulation therapy to a patient according to a plurality of different cycle settings over respective periods of time ("cycle time periods"). In some examples, the cycle time periods may each be on the order of days or even weeks. A cycle setting may define an on-cycle, during which electrical stimulation is delivered to the patient, and an off-cycle, during which electrical stimulation is not actively delivered to the patient, as well as the therapy parameter values with which the medical device generates and delivers electrical stimulation therapy to the patient. The cycle settings and cycle time periods may be selected such that the electrical stimulation therapy results in a response from the patient that reduces incontinence events, which may include involuntary voiding events, a reduction in the frequency of urge events, and the like.

Clause 1: In some examples, a method comprises determining, by processing circuitry, a first cycle setting for electrical stimulation therapy, wherein the first cycle setting defines a first on-cycle and a first off-cycle for the electrical stimulation therapy; determining, by the processing circuitry, a first cycle time period; controlling, by the processing circuitry, a medical device to deliver the electrical stimulation therapy to a patient according to the first cycle setting over the first cycle time period; determining, by the processing circuitry, a second cycle setting for the electrical stimulation therapy, wherein the second cycle setting defines a second on-cycle and a second off-cycle, wherein the second cycle setting is different from the first cycle setting; determining, by the processing circuitry, a second cycle time period; and controlling, by the processing circuitry, the medical device to deliver the electrical stimulation therapy to the patient according to the second cycle setting over the second cycle time period.

Clause 2: In some examples of the method of clause 1, the first cycle time period and the second cycle time period are equal.

Clause 3: In some examples of the method of clause 1, the first cycle time period and the second cycle time period are different.

Clause 4: In some examples of the method of any of clauses 1-3, at least one of the first on-cycle or the second on-cycle is selected to evoke a physiological response of the patient.

Clause 5: In some examples of the method of clause 4, the physiological response comprises a urinary sphincter contraction or a reduction in bladder contraction frequency.

Clause 6: In some examples of the method of any of clauses 1-5, at least one of the first off-cycle or the second off-cycle corresponds to a bladder fill time of the patient.

Clause 7: In some examples of the method of any of clauses 1-6, the electrical stimulation therapy is at or above a perception threshold of the patient.

Clause 8: In some examples of the method of any of clauses 1-6, the electrical stimulation therapy is below a perception threshold of the patient.

Clause 9: In some examples of the method of any of clauses 1-8, at least one of the first cycle time period or the second cycle time period is on the order of days.

Clause 10: In some examples of the method of any of clauses 1-9, at least one of the first on-cycle or the second on-cycle is about 10 minutes and at least one of the first off-cycle or the second off-cycle is about 10 minutes.

Clause 11: In some examples of the method of any of clauses 1-9, at least one of the first on-cycle or the second on-cycle is about 16 seconds and at least one of the first off-cycle or the second off-cycle is about 8 seconds.

Clause 12: In some examples of the method of any of clauses 1-9, at least one of the first on-cycle or the second on-cycle is about 30 minutes and at least one of the first off-cycle or the second off-cycle is about 26.5 hours.

Clause 13: In some examples of the method of any of clauses 1-12, the processing circuitry determines the first cycle setting or the second cycle setting based on one or more corresponding power consumption values.

Clause 14: In some examples of the method of any of clauses 1-13, determining, by the processing circuitry, the second cycle setting comprises pseudo-randomly selecting the second cycle setting from a plurality of predetermined cycle settings.

Clause 15: In some examples of the method of any of clauses 1-13, determining, by the processing circuitry, the second cycle setting comprises selecting a next cycle setting in an ordered list of cycle settings.

Clause 16: In some examples of the method of any of clauses 1-15, the second cycle time period follows the first cycle time period, and does not overlap with the first cycle time period.

Clause 17: In some examples, the method of any of clauses 1-16 further comprises determining, by the processing circuitry, a third cycle setting for the electrical stimulation therapy; and controlling, by the processing circuitry, a medical device to deliver the electrical stimulation therapy to the patient according to the third cycle setting prior to an end of the second cycle time period.

Clause 18: In some examples, the method of clause 17 further comprises determining, by the processing circuitry, a number of symptom-related events of the patient for a predetermined interval of time, wherein determining the third cycle setting comprises determining the third cycle setting in response to determining the number of symptom-related events for the predetermined interval of time is greater than or equal to a threshold value.

Clause 19: In some examples, a system comprises therapy delivery circuitry configured to generate and deliver electrical stimulation therapy to a patient; and processing circuitry configured to: determine a first cycle setting for electrical stimulation therapy, wherein the first cycle setting defines a first on-cycle and a first off-cycle, determine a first cycle time period, control the therapy delivery circuitry to deliver the electrical stimulation therapy according to the first cycle setting over the first cycle time period, determine a second cycle setting for the electrical stimulation therapy, wherein the second cycle setting defines a second on-cycle and a second off-cycle, wherein the second cycle setting is different from the first cycle setting, determine a second cycle time period, and control the therapy delivery circuitry to deliver the electrical stimulation therapy to the patient according to the second cycle setting over the second cycle time period.

Clause 20: In some examples of the system of clause 19, the first cycle time period and the second cycle time period are equal.

Clause 21: In some examples of the system of clause 19, the first cycle time period and the second cycle time period are different.

Clause 22: In some examples of the system of any of clauses 19-21, at least one of the first on-cycle or the second on-cycle is selected to evoke a physiological response of the patient.

Clause 23: In some examples of the system of clause 22, the physiological response comprises a urinary sphincter contraction or a reduction in bladder contraction frequency.

Clause 24: In some examples of the system of any of clauses 19-23, at least one of the first off-cycle or the second off-cycle corresponds to a bladder fill time of the patient.

Clause 25: In some examples of the system of any of clauses 19-24, the electrical stimulation therapy is at or above a perception threshold of the patient.

Clause 26: In some examples of the system of any of clauses 19-24, the electrical stimulation therapy is below a perception threshold of the patient.

Clause 27: In some examples of the system of any of clauses 19-26, at least one of the first cycle time period or the second cycle time period is on the order of days.

Clause 28: In some examples of the system of any of clauses 19-27, the processing circuitry is configured to determine the first cycle setting or the second cycle setting based on one or more corresponding power consumption values.

Clause 29: In some examples, the system of any of clauses 19-28 further comprises a memory storing a plurality of cycle settings, wherein the processing circuitry is configured to determine the second cycle setting by at least pseudo-randomly selecting the second cycle setting from the plurality of cycle settings.

Clause 30: In some examples, the system of any of clauses 19-28 further comprises a memory storing a plurality of cycle settings, wherein the processing circuitry is configured to determine the second cycle setting by at least selecting a next cycle setting in the ordered list of cycle settings.

Clause 31: In some examples of the system of any of clauses 19-30, the second cycle time period follows the first cycle time period, and does not overlap with the first cycle time period.

Clause 32: In some examples of the system of any of clauses 19-31, the processing circuitry is further configured to: determine a third cycle setting for the electrical stimulation therapy, and control the therapy delivery circuitry to deliver the electrical stimulation therapy to the patient according to the third cycle setting prior to an end of the second cycle time period.

Clause 33: In some examples, the system of clause 32 further comprises a memory that stores indications of symptom-related events of the patient, wherein the processing circuitry is further configured to determine a number of symptom-related events of the patient for a predetermined interval of time, and wherein the processing circuitry is configured to determine the third cycle setting in response to determining the number of symptom-related events for the predetermined interval of time is greater than or equal to a threshold value.

Clause 34: In some examples, a system comprises means for generating and delivering electrical stimulation to a patient; means for determining a first cycle setting for electrical stimulation therapy, wherein the first cycle setting defines a first on-cycle and a first off-cycle for the electrical stimulation therapy; means for determining a first cycle time period; means for controlling the means for generating and deliver electrical stimulation to deliver the electrical stimulation therapy to a patient according to the first cycle setting over the first cycle time period; means for determining a second cycle setting for the electrical stimulation therapy, wherein the second cycle setting defines a second on-cycle and a second off-cycle, wherein the second cycle setting is different from the first cycle setting; means for determining a second cycle time period; and means for controlling the means for generating and deliver electrical stimulation to deliver the electrical stimulation therapy to the patient according to the second cycle setting over the second cycle time period.

Clause 35: In some examples of the system of clause 34, the means for determining the second cycle setting comprises means for pseudo-randomly selecting the second cycle setting from a plurality of predetermined cycle settings.

Clause 36: In some examples of the system of any of clauses 34 and 35, the means for determining the second cycle setting comprises means for selecting a next cycle setting in an ordered list of cycle settings.

Clause 37: In some examples, a non-transitory computer-readable storage medium comprises instructions that, when executed by processing circuitry, cause the processing circuitry to: determine a first cycle setting for electrical stimulation therapy, wherein the first cycle setting defines a first on-cycle and a first off-cycle; determine a first cycle time period; control a medical device to deliver the electrical stimulation therapy according to the first cycle setting over the first cycle time period; determine a second cycle setting for the electrical stimulation therapy, wherein the second cycle setting defines a second on-cycle and a second off-cycle, wherein the second cycle setting is different from the first cycle setting; determine a second cycle time period; and control the medical device to deliver the electrical stimulation therapy to the patient according to the second cycle setting over the second cycle time period.

Clause 38: In some examples, a method comprises determining, by processing circuitry, a cycle setting for electrical stimulation therapy, wherein the cycle setting defines an on-cycle and an off-cycle for the electrical stimulation therapy, and wherein determining the cycle setting comprises pseudo-randomly selecting the cycle setting from a plurality of predetermined cycle settings; determining, by the processing circuitry, a cycle time period; and controlling, by the processing circuitry, a medical device to deliver the electrical stimulation therapy to a patient according to the cycle setting over the cycle time period.

Clause 39: In some examples of the method of clause 38, the cycle setting comprises a first cycle setting defining a first on-cycle and a first off-cycle, and the cycle time period is a first cycle time period, the method further comprising: determining, by processing circuitry, a second cycle setting for the electrical stimulation therapy, wherein the second cycle setting defines a second on-cycle and a second off-cycle, and wherein determining the second cycle setting comprises pseudo-randomly selecting the second cycle setting from the plurality of predetermined cycle settings; determining, by the processing circuitry, a second cycle time period; and controlling, by the processing circuitry, the therapy delivery circuitry to deliver the electrical stimulation therapy to the patient according to the second cycle setting over the second cycle time period.

Clause 40: In some examples, a system comprises therapy delivery circuitry configured to generate and deliver electrical stimulation to a patient; and processing circuitry configured to: determine a cycle setting for electrical stimulation therapy, wherein the cycle setting defines an on-cycle and an off-cycle for the electrical stimulation therapy, and wherein determining the cycle setting comprises pseudo-randomly selecting the cycle setting from a plurality of predetermined cycle settings, determine a cycle time period, and control the therapy delivery circuitry to deliver the electrical stimulation therapy to the patient according to the cycle setting over the cycle time period.

Clause 41: In some examples of the system of clause 40, the cycle setting comprises a first cycle setting defining a first on-cycle and a first off-cycle, and the cycle time period is a first cycle time period, the processing circuitry being further configured to: determine a second cycle setting for the electrical stimulation therapy by at least pseudo-randomly selecting the second cycle setting from the plurality of predetermined cycle settings, wherein the second cycle setting defines a second on-cycle and a second off-cycle, determine a second cycle time period, and control the therapy delivery circuitry to deliver the electrical stimulation therapy to the patient according to the second cycle setting over the second cycle time period.

Clause 42: In some examples, a system comprises means for generating and delivering electrical stimulation to a patient; means for pseudo-randomly selecting a cycle setting for electrical stimulation therapy from a plurality of predetermined cycle settings, wherein the cycle setting defines an on-cycle and an off-cycle for the electrical stimulation therapy; means for determining a cycle time period; and means for controlling the means for generating and delivering electrical stimulation to a patient to deliver the electrical stimulation therapy to a patient according to the cycle setting over the cycle time period.

Clause 43: In some examples, a method comprises determining, by processing circuitry, a first reminder program for electrical stimulation, the first reminder program defining one or more electrical stimulation parameter values for delivery of electrical stimulation to a patient; controlling, by the processing circuitry, a medical device to deliver reminder electrical stimulation to the patient according to the first reminder program, wherein the reminder electrical stimulation is above a perception threshold of the patient; determining, by the processing circuitry, a second reminder program for electrical stimulation, the second reminder program defining one or more electrical stimulation parameter values, wherein at least one of the one or more electrical stimulation parameter values of the second reminder program is different from the one or more electrical stimulation parameter values of the first reminder program; and controlling, by the processing circuitry, the medical device to deliver the reminder electrical stimulation to the patient according to the second reminder program.

Clause 44: In some examples of the method of clause 43, the first reminder program comprises a daytime sub-program and a nighttime sub-program, and wherein controlling the medical device to deliver the reminder electrical stimulation to the patient according to the first reminder program comprises: determining the patient is asleep; in response to determining the patient is asleep, controlling, by the processing circuitry, the medical device to deliver the reminder electrical stimulation to the patient according to the nighttime sub-program; determining the patient is awake; and in response to determining the patient is awake, controlling, by the processing circuitry, the medical device to deliver the reminder electrical stimulation to the patient according to the daytime sub-program.

Clause 45: In some examples, a system comprises therapy delivery circuitry configured to generate and deliver electrical stimulation to a patient; and processing circuitry configured to: determine a first reminder program for electrical stimulation, the first reminder program defining one or more electrical stimulation parameter values for delivery of electrical stimulation to a patient; control the therapy delivery circuitry to deliver reminder electrical stimulation to the patient according to the first reminder program, wherein the reminder electrical stimulation is above a perception threshold of the patient; determine a second reminder program for electrical stimulation, the second reminder program defining one or more electrical stimulation parameter values, wherein at least one of the one or more electrical stimulation parameter values of the second reminder program is different from the one or more electrical stimulation parameter values of the first reminder program; and control the therapy delivery circuitry to deliver the reminder electrical stimulation to the patient according to the second reminder program.

Clause 46: In some examples of the system of clause 45, the first reminder program comprises a daytime sub-program and a nighttime sub-program, and wherein the processing circuitry is configured to control the therapy delivery circuitry to deliver the reminder electrical stimulation to the patient according to the first reminder program by at least: determining the patient is asleep, in response to determining the patient is asleep, controlling, by the processing circuitry, the medical device to deliver the reminder electrical stimulation to the patient according to the nighttime sub-program, determining the patient is awake, and in response to determining the patient is awake, controlling, by the processing circuitry, the medical device to deliver the reminder electrical stimulation to the patient according to the daytime sub-program.

Clause 47: In some examples, a system comprises means for generating and delivering electrical stimulation to a patient; means for determining a first reminder program for electrical stimulation, the first reminder program defining one or more electrical stimulation parameter values for delivery of electrical stimulation to a patient; means for controlling the means for generating and delivering electrical stimulation to deliver reminder electrical stimulation to the patient according to the first reminder program, wherein the reminder electrical stimulation is above a perception threshold of the patient; means for determining a second reminder program for electrical stimulation, the second reminder program defining one or more electrical stimulation parameter values, wherein at least one of the one or more electrical stimulation parameter values of the second reminder program is different from the one or more electrical stimulation parameter values of the first reminder program; and means for controlling the means for generating and delivering electrical stimulation to deliver the reminder electrical stimulation to the patient according to the second reminder program.

Clause 48: In some examples of the system of clause 47, the first reminder program comprises a daytime sub-program and a nighttime sub-program, further comprising: means for determining whether the patient is asleep or awake, wherein the means for controlling the means for generating and delivering electrical stimulation to deliver reminder electrical stimulation to the patient according to the first reminder program controls the medical device to deliver the reminder electrical stimulation to the patient according to the nighttime sub-program in response to the means for determining the patient is asleep, and controls the medical device to deliver the reminder electrical stimulation to the patient according to the daytime sub-program in response to the means for determining the patient is awake.

Clause 49: In some examples, a non-transitory computer-readable storage medium comprises instructions that, when executed by processing circuitry, cause the processing circuitry to: determine a first reminder program for electrical stimulation, the first reminder program defining one or more electrical stimulation parameter values for delivery of electrical stimulation to a patient; control a medical device to deliver reminder electrical stimulation to the patient according to the first reminder program, wherein the reminder electrical stimulation is above a perception threshold of the patient; determine a second reminder program for electrical stimulation, the second reminder program defining one or more electrical stimulation parameter values, wherein at least one of the one or more electrical stimulation parameter values of the second reminder program is different from the one or more electrical stimulation parameter values of the first reminder program; and control the medical device to deliver the reminder electrical stimulation to the patient according to the second reminder program.

The details of one or more aspects of the disclosure are set forth in the accompanying drawings and the description below.

Figure 1:
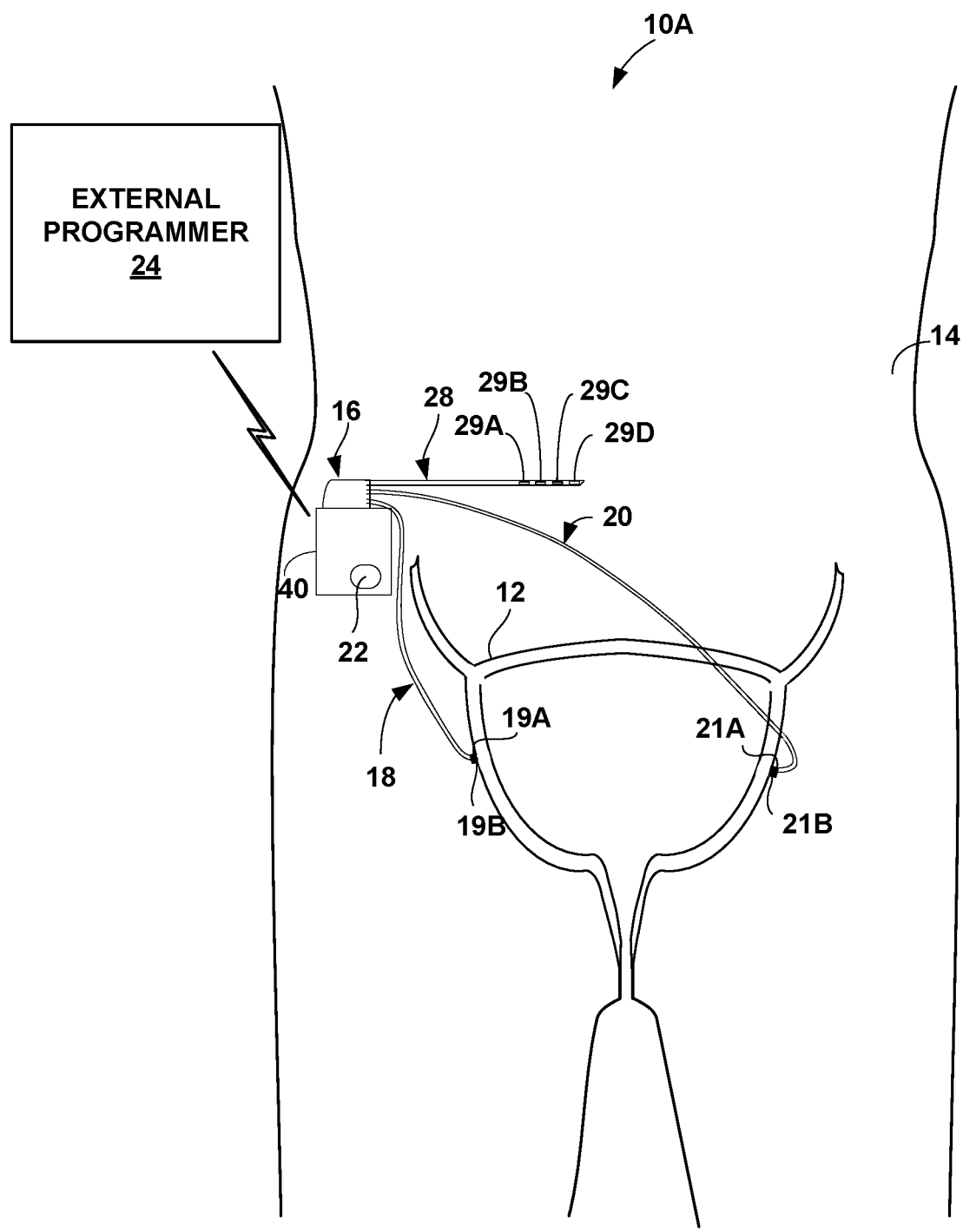
FIG. 1 illustrates, diagrammatically, a patient with an example implanted medical device including a therapy delivery circuitry.

The details of one or more examples of this disclosure are set forth in the accompanying drawings and the description below. Other features, objects, and advantages of this disclosure will be apparent from the description and drawings, and from the claims.

DETAILED DESCRIPTION

As described above, devices, systems, and techniques for managing incontinence (e.g., urinary incontinence and/or fecal incontinence) of a patient and/or other patient conditions using electrical stimulation are described in this disclosure. In some examples, a medical device is configured to deliver electrical stimulation to a patient for a period of time using a predetermined cycling setting in order to decrease the number of episodes of incontinence (also referred to herein as incontinence events) or the degree of urgency associated with the incontinence experienced by the patient over time. For example, the medical device may be configured to deliver electrical stimulation to a patient using a plurality of different cycling settings, each for a respective cycle time period to provide efficacious electrical stimulation therapy to the patient to manage a patient condition.

Urinary incontinence refers to a condition of involuntary loss of urine, and may include urge urinary incontinence, stress incontinence, or both stress and urge incontinence, which may be referred to as mixed urinary incontinence. As used in this disclosure, the term "urinary incontinence" includes disorders in which urination occurs when not desired, such as stress or urge incontinence, disorders in which urination does not occur as desired, such as urinary retention disorder, and overactive bladder. Symptoms of overactive bladder may include one or more of urge incontinence, frequent urination, and urgency (frequent urges to urinate). While urinary incontinence is primarily referred to herein, the devices, systems, and techniques described herein may also be used to manage a fecal incontinence condition of a patient.

Electrical stimulation therapy may include delivery of electrical stimulation to one or more target tissue sites proximate to one or more peripheral nerves (e.g., the sacral, pudendal, dorsal-genital, and tibial nerves, and branches thereof) via a medical device to modulate activity of the one or more peripheral nerves. Such electrical stimulation may be used to modify pelvic floor function to manage various patient conditions (e.g., urinary incontinence and fecal incontinence). Although the present disclosure describes the delivery of electrical stimulation therapy by an implantable medical device (IMD), the devices, systems, and techniques of the present disclosure also may be implemented by an external medical device that delivers electrical stimulation therapy via implanted or external electrodes.

Some medical device systems for delivering electrical stimulation therapy to a patient for the management of a urinary or fecal incontinence condition may deliver continuous electrical stimulation according to a selected therapy program. For example, the medical system may deliver electrical stimulation therapy to a patient for according to a selected therapy program for an indefinite duration of time. Although these therapies for treating urinary incontinence may be effective, symptoms such as involuntary urination events or unwanted urinary retention still may occur, or may recur over time. In some cases, such recurring symptoms may be attributable to the adaptation of the patient to the electrical stimulation therapy, such that electrical stimulation therapy according to the selected therapy program no longer provides efficacious management of the patient's incontinence condition. In addition, or instead, residual symptoms may be attributable to a lack of patient cognizance of a need to void, which may result in involuntary voiding events.

In contrast to medical device systems in which electrical stimulation therapy is delivered to a patient according to a selected therapy program for an indefinite period of time, a medical device system that is configured to deliver electrical stimulation therapy to a patient according to a plurality of cycle settings is described herein. A therapy program may define a cycle setting as well as electrical stimulation parameter values that define the electrical stimulation signal (e.g., an amplitude, pulse width, and pulse rate). A cycle setting may, for example, define the duty cycle of electrical stimulation therapy. The duty cycle indicates an "on" time of electrical stimulation therapy (e.g., when electrical stimulation is actively being delivered to the patient) and an "off" time of electrical stimulation therapy (e.g., when no electrical stimulation is actively being delivered by a medical device to the patient). The cycle setting may, therefore, define an on-cycle, which may be the duration of time over which electrical stimulation therapy is delivered to a patient, and an off-cycle, which may be the duration of time over which electrical stimulation therapy is not delivered. The on-cycles and off-cycles may be alternated during a cycle time period, which may be a time period over which the medical device delivers electrical stimulation therapy to the patient according to a particular cycle setting.

A therapy program including a cycle setting may be used by processing circuitry of a medical system (e.g., of a medical device or a medical device programmer) to control delivery of electrical stimulation therapy by the medical device (e.g., via one or more electrodes), and may include information identifying which electrodes have been selected for delivery of stimulation according to the therapy program, the polarities of the selected electrodes, i.e., the electrode configuration for the program, the voltage or current amplitude and frequency of electrical stimulation delivered by the electrodes, and the cycle setting for controlling the timing of the delivery of an electrical stimulation signal. In the case of electrical stimulation pulses, the therapy program may include a pulse rate, and a pulse width. Delivery of electrical stimulation pulses will be described for purposes of illustration. However, electrical stimulation may be delivered in other forms such as continuous waveforms.

In some examples, the delivery of electrical stimulation therapy according to one or more cycle settings may help to reduce the recurring or residual symptoms described above. For example, a change in the cycle setting according to which electrical stimulation therapy is delivered may reduce patient adaptation to the delivered stimulation, which may help prolong the efficacy of the electrical stimulation therapy delivered by a medical device.

As described herein, each cycle setting may include a value of an on-cycle and a value of an off-cycle. In some examples, the value of the on-cycle may be referred to as "time X," or simply as "X." During time X of a cycle setting, electrical stimulation may be actively delivered as pulses or bursts of pulses. Thus, although there may be a period of time during time X in which an electrical stimulation signal has an amplitude of about 0 (e.g., between pulses or bursts of pulses), the electrical stimulation signal may still be considered to be actively delivered during time X. The value of the off-cycle may be referred to as "time Y," or simply as "Y." During time Y, a medical device is not actively delivering an electrical stimulation signal to the patient. Together, the values of time X and time Y define the overall duration of a therapy cycle.

During a cycle time period (e.g., a period of days or even weeks), when a medical device is delivering electrical stimulation therapy to a patient according to a particular cycle setting, the medical device may deliver electrical stimulation therapy to a patient according to a plurality of repeating therapy cycles (e.g., according to a plurality of alternating time Xs and time Ys). For example, there may be a time X followed by a time Y, followed by a time X, followed by a time Y, and so forth through the cycle time period.

In some examples, a medical device may deliver the electrical stimulation therapy according to a first cycle setting over the course of a cycle time period. A cycle time period may be a predetermined duration of time for delivery of electrical stimulation therapy according to a particular cycle setting. The cycle period can be, for example, on the order of days (e.g., seven days, 10 days, and the like) or even weeks (e.g., two weeks, four weeks, six weeks, or eight weeks). At the end of a cycle time period, the medical device may deliver electrical stimulation according a combination of any number of additional cycle settings, which may be different from the first cycle setting, over respective cycle time periods. In this manner, the devices, systems, and techniques that are configured to deliver electrical stimulation therapy according to one or more cycle settings may provide improved patient outcomes over some systems that may only be configured to deliver continuous electrical stimulation therapy according to a therapy program over an indefinite period of time. For example, it is has been determined that, in some cases, the use of a single cycle setting or a plurality of cycle settings may help to reduce the number of incontinence episodes that the patient may experience over a given period of time. A medical device may deliver electrical stimulation to a patient using a combination of any number of the available cycling settings over a certain number of days or hours.

As examples of cycle settings, a first cycle setting may define an on-cycle of about 16 seconds (e.g., 16 seconds or nearly 16 seconds) and an off-cycle of about 8 seconds (e.g., 8 seconds or nearly 8 seconds), and a first cycle time period may be about 28 days (e.g., 28 days or nearly 28 days). In this example, a medical device implementing the first cycle setting turns electrical stimulation on for 16 seconds and off for 8 seconds repeatedly over a 28 day period of time. A second cycle setting may, for example, define an on-cycle of about 10 minutes and an off-cycle of about 10 minutes, and a second cycle time period may be about 28 days. In this example, a medical device implementing the second cycle setting turns electrical stimulation on for about 10 minutes and off for about 10 minutes repeatedly over a 28 day period of time. In a third example cycle setting, a third cycle setting may define an on-cycle of about 30 seconds and an off-cycle of about 23.5 hours, and a third cycle time period may be about 28 days. In this example, a medical device implementing the third cycle setting turns electrical stimulation on for 30 minutes and off for 23.5 hours repeatedly over a 28 day period of time. However, it is understood that other cycle settings associated with delivery of the electrical stimulation may also be utilized.

In examples described herein, a cycle setting may be determined (e.g., selected from a plurality of stored cycle settings) by processing circuitry of a medical device or another device (e.g., a medical device programmer), and used by the processing circuitry of the medical device or another device to control the delivery of electrical stimulation therapy by the medical device via one or more electrodes.

In addition to or instead of the therapy delivery according to one or more cycle settings, in some examples described herein, a medical device may deliver electrical stimulation that the patient can perceive, which may serve as a reminder to the patient that he or she may need to void, or as a reminder to the patient that he or she is receiving electrical stimulation therapy. This may be referred to as "reminder electrical stimulation." As discussed in further detail below, reminder electrical stimulation may further improve patient outcomes over some systems that do not provide such reminders. The electrical stimulation delivered as a reminder may or may not evoke a physiological response from the patient that helps reduce incontinence events. Examples of such physiological responses include, but are not limited to, contraction of the urethral sphincter of the patient, reduction in the bladder contraction frequency of the patient, and the like.

In the examples described herein, a medical device may deliver electrical stimulation therapy to treat one more patient conditions associated with the urinary bladder and associated portions of the nervous system. Although examples of the disclosure primarily are described with respect to managing patient conditions such as urge incontinence, urinary incontinence, or urine retention, the devices, systems, and techniques described herein may be configured to manage other patient conditions, such as overactive bowel, irritable bowel, pelvic pain, urgency frequency, bowel pain, bladder pain, and the like. For example, the devices, systems, and techniques described herein may be applied to the delivery of electrical stimulation to inhibit bowel contraction, e.g., in a manner that treats a bowel condition, such as fecal incontinence or irritable bowel syndrome. In any such examples, the patient may experience a reduction in the symptoms associated with the patient condition that the delivered electrical stimulation therapy is configured to manage.

FIG. 1 is a conceptual diagram illustrating an example therapy system 10A that delivers electrical stimulation therapy to a patient 14 to manage an urgency and/or urinary incontinence disorder of patient 14. Therapy system 10A is an example of a therapy system configured to implement the techniques described herein for delivering electrical stimulation therapy according to one or more cycle settings (e.g., two or more cycle settings), delivering reminder electrical stimulation, or delivering both reminder electrical stimulation and electrical stimulation therapy according to one or more cycle settings. Therapy system 10A includes an implantable medical device (IMD) 16, which is coupled to leads 18, 20, and 28, sensing circuitry 22, and external programmer 24. IMD 16 generally operates as a therapy device configured to generate and deliver electrical stimulation to, for example, a tissue site proximate a pelvic floor nerve, a pelvic floor muscle, the urinary sphincter, a detrusor muscle, or other pelvic floor targets. Pelvic floor nerves include peripheral nerves such as sacral nerves, pudendal nerves and associated branches, and dorsal genital nerves. In some examples, IMD 16 delivers the electrical stimulation therapy to a sacral nerve of patient 14 to inhibit bladder contractions.

IMD 16 is configured to provide electrical stimulation therapy to patient 14 by generating and delivering electrical stimulation signals to a target therapy site within patient 14 by lead 28 and, more particularly, via electrodes 29A-29D (collectively referred to as "electrodes 29"), which can be disposed proximate to a distal end of lead 28 in some examples. For example, IMD 16 may deliver electrical stimulation therapy to patient 14 according to one or more cycle settings. For example, IMD 16 may deliver electrical stimulation therapy to patient 14 according to a first cycle setting for a first cycle time period, which may be on the order of days or weeks in some examples. At the expiration of the first cycle time period, IMD 16 may select a second cycle setting that is different from the first cycle setting, and stop delivering of electrical stimulation according to the first cycle setting and deliver electrical stimulation therapy to patient 14 according to the second cycle setting for a second cycle time period, which may be the same or different from the first cycle time period. The second cycle time period may follow immediately after the first cycle time period, and may not overlap in time. In some cases, it may be advantageous for IMD 16 to deliver electrical stimulation therapy to patient 14 according to cycle settings that are changed periodically. For example, as noted above, the delivery of electrical stimulation therapy according to varied cycle settings may increase the overall efficacy of the electrical stimulation therapy delivered to patient 14, such as by reducing a number or frequency of involuntary voiding events.

In some examples, in addition to the delivery of electrical stimulation therapy according to one or more cycle settings, IMD 16 may deliver the electrical stimulation to patient 14 based on, e.g., sensor data and/or patient input. As one example, IMD 16 may detect a bladder contraction based on sensor data and then deliver electrical stimulation based on the detected bladder contraction. As another example, patient 14 may use external programmer 24 to provide input to IMD 16, e.g., indicating an increased probability of unintentional voiding, and IMD 16 may deliver the electrical stimulation to patient 14 to inhibit bladder contraction based on the patient input.

In some examples, in addition to electrical stimulation therapy, IMD 16 may also be configured to provide reminder electrical stimulation to patient 14 by generating and delivering electrical stimulation signals to a target therapy site by lead 28 and, more particularly, via one or more selected electrodes 29. The reminder electrical stimulation may be referred to as electrical reminder therapy. For example, IMD 16 may deliver the reminder electrical stimulation to patient 14 at predetermined intervals and in the form of reminder pulses. In some examples, reminder electrical stimulation may include the delivery of electrical signals to a target therapy site for the purpose of reminding patient 14 to voluntarily void, or for the purpose of reminding patient 14 of the existence of the electrical stimulation therapy (e.g., reminding patient 14 that IMD 16 is implanted in patient 14 and delivers electrical stimulation therapy to patient 14). As discussed below in greater detail, providing reminder electrical stimulation may result in an improvement in the efficacy of the electrical stimulation therapy provided to patient 14 by IMD 16, thereby resulting in fewer symptom-related events, such as incontinence events.

IMD 16 may be surgically implanted in patient 14 at any suitable location within patient 14, such as near the pelvis. In some examples, the implantation site may be a subcutaneous location in the side of the lower abdomen or the side of the lower back or upper buttocks. IMD 16 has biocompatible housing 30, which may be formed from titanium, stainless steel, a liquid crystal polymer, or the like. The proximal ends of leads 18, 20, and 28 are electrically and mechanically coupled to IMD 16 either directly or indirectly, e.g., via one or more respective lead extensions. Electrical conductors disposed within the lead bodies of leads 18, 20, and 28 electrically connect sense electrodes (not shown) and stimulation electrodes, such as electrodes 29, to a therapy delivery circuitry (e.g., a stimulation generator) within IMD 16. In the example of FIG. 1, leads 18 and 20 carry electrodes 19A, 19B (collectively referred to as "electrodes 19") and electrodes 21A, 21B (collectively referred to as "electrodes 21"), respectively. As described in a further detail below, electrodes 19 and 21 may be positioned for sensing an impedance of bladder 12, which may decrease as the volume of urine within bladder 12 increases.

One or more medical leads, e.g., leads 18, 20, and 28, may be connected to IMD 16, and may be surgically or percutaneously tunneled to position one or more electrodes carried by a distal end of the respective lead at a desired pelvic nerve or muscle site, e.g., one of the previously listed target therapy sites such as a sacral or pudendal nerve. In some examples, therapy system 10A includes one or more additional leads that each include one or more electrodes for sensing one or more physiological parameters, or one or more other types of sensors for sensing one or more physiological parameters. For example, in FIG. 1, leads 18 and 20 are placed proximate to an exterior surface of the wall of bladder 12 at first and second locations, respectively. Electrodes 29 of the common lead 28 may deliver stimulation to the same or different nerves. In other examples of therapy system 10, IMD 16 may be coupled to more than one lead, each of which may include one or more electrodes for the delivery of electrical stimulation to different stimulation sites within patient 14, e.g., to target different nerves.

In the example shown in FIG. 1, leads 18, 20, and 28 are cylindrical. Electrodes 19, 21, and 29 of leads 18, 20, and 28, respectively, may be ring electrodes, segmented electrodes, or partial ring electrodes. Segmented and partial ring electrodes each extend along an arc less than 360 degrees (e.g., 90-120 degrees) around the outer perimeter of the respective lead 18, 20, 28. In some examples, one or more of leads 18, 20, and 28 may be, at least in part, paddle-shaped (i.e., a "paddle" lead), and may include pad electrodes positioned on a distal paddle surface.

In some examples, one or more of electrodes 19, 21, and 29 may be cuff electrodes that are configured to extend at least partially around a nerve (e.g., extend axially around an outer surface of a nerve). Depending on the target therapy delivery site and the particular patient, delivery of electrical stimulation by IMD 16 via one or more cuff electrodes, and/or segmented electrodes, may help achieve a more uniform electrical field or activation field distribution relative to the target nerve, thereby minimizing discomfort to patient 14 that may result from the delivery of electrical stimulation therapy.

The illustrated numbers and configurations of leads 18, 20, and 28 and the electrodes carried thereon are merely one example. Other configurations that may include various numbers and positions of the leads and electrodes also are possible. For example, IMD 16 may be coupled to additional leads or lead segments having one or more electrodes positioned at different locations in the pelvic region of patient 14. The additional leads may be used for delivering stimulation therapies to respective stimulation sites within patient 14, or may be used for monitoring one or more physiological parameters of patient 14. In examples in which the target therapy sites for the stimulation therapies are different, IMD 16 may be coupled to two or more leads, as may be required for bilateral or multi-lateral stimulation. In another example, IMD 16 may be coupled to fewer leads, e.g., to lead 28 only.

In some examples, IMD 16 may deliver electrical stimulation therapy based on patient input. In some examples, patient 14 may provide patient input using external programmer 24, or by tapping on the surface of the skin located over IMD 16, when IMD 16 includes a motion sensor that is responsive to tapping. In such examples, patient 14 may provide input to IMD 16 that indicates an urge felt by the patient, a leakage incident experienced by the patient, an imminent voiding event predicted by the patient, or a voluntary voiding event to be undertaken by the patient. In this way, therapy system 10A may provide patient 14 with direct control of the stimulation therapy delivered by IMD 16, which may improve the physiological and/or psychological treatment outcomes of patient 14.

In the illustrated example of FIG. 1, IMD 16 determines an impedance through bladder 12, which may vary as a function of the volume of urine present in bladder 12 and the contraction state of bladder 12. In such examples, the impedance of bladder 12 may be sensed via electrodes 19 and 21, which may be positioned on leads 18 and 20, respectively. In the example shown in FIG. 1A, IMD 16 determines bladder impedance using a four-wire (or Kelvin) measurement technique. In other examples, IMD 16 may measure bladder impedance using a two-wire sensing arrangement. In either case, IMD 16 may transmit an electrical measurement signal; e.g., a current, through bladder 12 via leads 18 and 20, and determine bladder impedance based on a measured value of the transmitted electrical signal.

In the exemplary four-wire arrangement shown in FIG. 1, electrodes 19A and 21A and electrodes 19B and 21B may be located substantially opposite each other relative to the center of bladder 12. For example, electrodes 19A and 21A may be placed on opposing sides of bladder 12, either anterior and posterior or left and right. In FIG. 1, electrodes 19A, 19B and 21A, 21B are shown placed proximate to an exterior surface of the wall of bladder 12. In other examples, electrodes 19A, 19B and 21A, 21B may be sutured or otherwise affixed to the bladder wall, or may be implanted within the bladder wall. To measure the impedance of bladder 12, IMD 16 may source an electrical signal, such as an electrical current, to electrode 19A via lead 18, while electrode 21A via lead 20 sinks the electrical signal. IMD 16 then may determine a voltage measurement between electrodes 19B and 21B via leads 18 and 20, respectively. IMD 16 then may determine the impedance of bladder 12 using a known value of the electrical signal sourced and the determined voltage.

In the example of FIG. 1, IMD 16 includes a sensor comprising sensing circuitry 22 for detecting changes in the contraction of bladder 12. Sensing circuitry 22 may include, for example, one or more pressure sensors configured to detect changes in bladder pressure, one or more electrodes for sensing pudendal or sacral afferent nerve signals, one or more electrodes for sensing detrusor muscle or urinary sphincter EMG signals, or any combination thereof. In some examples, sensing circuitry 22 may include one or more remote pressure sensors that wirelessly transmits signals to IMD 16, or may include one or more pressure sensors positioned on one or more of leads 18, 20, and 28. In such examples, a pressure sensor may include a detrusor pressure sensor or a sphincter pressure sensor. Such sensors may be configured to sense a contraction of a detrusor muscle or urethral sphincter of bladder 12 as an indication of a bladder fill level, patient sensation of an urge to void or other sensation related to voiding, or other physiological indication of bladder function. In other examples, sensing circuitry 22 may include one or more sense electrodes configured to sense afferent nerve signals. In such examples, the sense electrodes may be positioned on one or more of leads 18, 20, and 28. In examples in which sensing circuitry 22 includes one or more electrodes configured to sense a detrusor muscle or urinary sphincter EMG, such electrodes may be carried on one or more of leads 18, 20, and 28. In any of the examples described above, IMD 16 may control the delivery of electrical stimulation based on input received from bladder sensing circuitry 22. For example, IMD 16 may initiate the delivery of electrical stimulation to inhibit the contraction of bladder 12 when sensing circuitry 22 indicates an increase in the probability of an involuntary voiding event of patient 14, such as when an increase in bladder pressure or a change in muscle activity is detected by sensing circuitry 22.

In other examples, sensing circuitry 22 may include a patient motion sensor that generates a signal indicative of patient activity level or posture state. In some examples, in addition to delivering electrical stimulation therapy according to the one or more cycle settings, IMD 16 controls the delivery of stimulation therapy to patient 14 based on a sensed patient activity level or a patient posture state. For example, a patient activity level that is greater than or equal to a threshold may indicate that there is an increase in urgency and/or an increase in the probability that an incontinence event will occur, and accordingly, IMD 16 may provide electrical stimulation based on the patient activity level. In one example, the IMD 16 may deliver electrical stimulation to inhibit bladder contractions in response to a patient activity level that is greater than a threshold value, since there may be an increase in urgency and/or an increase in the probability that an incontinence event may occur. The inhibition of bladder contractions due to the delivery of electrical stimulation may reduce the probability that an incontinence event may occur.

As an additional example, patient 14 may be more prone to an incontinence event when in an upright posture state compared to a horizontal (i.e., lying down) posture state. Accordingly, in some examples, IMD 16 may be configured to deliver electrical stimulation to patient 14 based on the patient posture state sensed by sensing circuitry 22. For example, IMD 16 may deliver electrical stimulation to inhibit bladder contractions when sensing circuitry 22 senses that patient 14 is in a posture that is more prone to an incontinence event in order reduce the probability of an incontinence event.

As another example, sensing circuitry 22 may generate a signal indicative of patient motion. Processing circuitry of IMD 16 or programmer 24 then may determine, based on a pattern in the motion signal and/or other sensed parameters (e.g., bladder impedance), whether patient 14 voluntarily voided, involuntarily voided, or that an involuntary voiding event may be imminent.

Additionally, in other examples, sensing circuitry 22 may include a motion sensor that detects patient input, such as patient 14 tapping over the location in which IMD 16 is implanted, and causes processing circuitry of IMD 16 to control IMD 16 to deliver or suspend electrical stimulation therapy based on the patient input. In such examples, the processing circuitry may be configured to recognize various motion patterns, each of which may be associated with different inputs. For example, sensing circuitry 22 may be configured to detect a predetermined number or pattern of taps indicative of patient request, such as a request to suspend electrical stimulation therapy or a request to deliver electrical stimulation therapy. In other examples, such input may be received by programmer 24 and transmitted to processing circuitry of IMD 16.

System 10A includes an external programmer 24, as shown in FIG. 1. In some examples, programmer 24 may be a wearable communication device, handheld computing device, computer workstation, or networked computing device. As described in further detail below with respect to FIG. 4, programmer 24 may include a user interface that receives input from a user (e.g., patient 14, a patient caretaker or a clinician). The user interface may include a keypad and a display (e.g., an LCD display). The keypad may take the form of an alphanumeric keypad or a reduced set of keys associated with particular functions of programmer 24. Programmer 24 can additionally or alternatively include a peripheral pointing device, such as a mouse, via which a user may interact with the user interface. In some examples, a display of programmer 24 may include a touch screen display, and a user, such as patient 14, a caregiver, or a clinician, may interact with programmer 24 via the touch screen display. It should be noted that the user may also interact with programmer 24 and/or IMD 16 remotely via a networked computing device.

IMD 16 and programmer 24 may communicate via wireless communication using any techniques known in the art. Examples of communication techniques may include, for example, include radiofrequency (RF) telemetry, which may be an RF link established via an antenna according to Bluetooth, WiFi, or medical implant communication service (MICS), although other techniques are also contemplated. In some examples, programmer 24 may include a programming head that may be placed proximate to the patient's body near the IMD 16 implant site, in order to improve the quality or security of communication between IMD 16 and programmer 24.

In some examples, patient 14 may interact with programmer 24 to control IMD 16 to deliver the stimulation therapy, to manually abort the delivery of the stimulation therapy by IMD 16 while IMD 16 is delivering the therapy or is about to deliver the therapy, or to inhibit the delivery of the stimulation therapy by IMD 16, e.g., during voluntary voiding events. Patient 14 may, for example, use a keypad or touch screen of programmer 24 to cause IMD 16 to deliver the stimulation therapy, such as when patient 14 senses that a leaking episode may be imminent. In this way, patient 14 may use programmer 24 to control the delivery of the stimulation therapy "on demand," e.g., when extra stimulation therapy is desirable.

In some examples, patient 14 may interact with programmer 24 to terminate the delivery of the stimulation therapy during voluntary voiding events, or to modify the type of stimulation therapy that is delivered (e.g., to control IMD 16 to deliver stimulation therapy to help patient 14 voluntarily void in examples in which patient 14 has a urinary retention disorder). That is, patient 14 may use programmer 24 to enter input that indicates the patient will be voiding voluntarily. When IMD 16 receives the input from programmer 24, IMD 16 may suspend delivery the stimulation therapy for a predetermined period of time, e.g., two minutes, to allow the patient to voluntarily void, or switch to a different type of stimulation therapy to help patient 14 voluntarily void.

A user, such as a physician, technician, surgeon, electrophysiologist, or other clinician, may also interact with programmer 24 or another separate programmer (not shown), such as a clinician programmer, to communicate with IMD 16. Such a user may interact with a programmer to retrieve physiological or diagnostic information from IMD 16. The user may also interact with a programmer to program IMD 16, e.g., select values for the stimulation parameter values of one or more cycle settings with which IMD 16 generates and delivers electrical stimulation and/or the other operational parameters of IMD 16. For example, the user may use programmer 24 to retrieve information from IMD 16 regarding the contraction of bladder 12 and voiding events, including data contained in a voiding diary stored by IMD 16. As another example, the user may use programmer 24 to retrieve information from IMD 16 regarding the performance or integrity of IMD 16 or other components of system 10A, such as leads 18, 20, and 28, or a power source of IMD 16.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
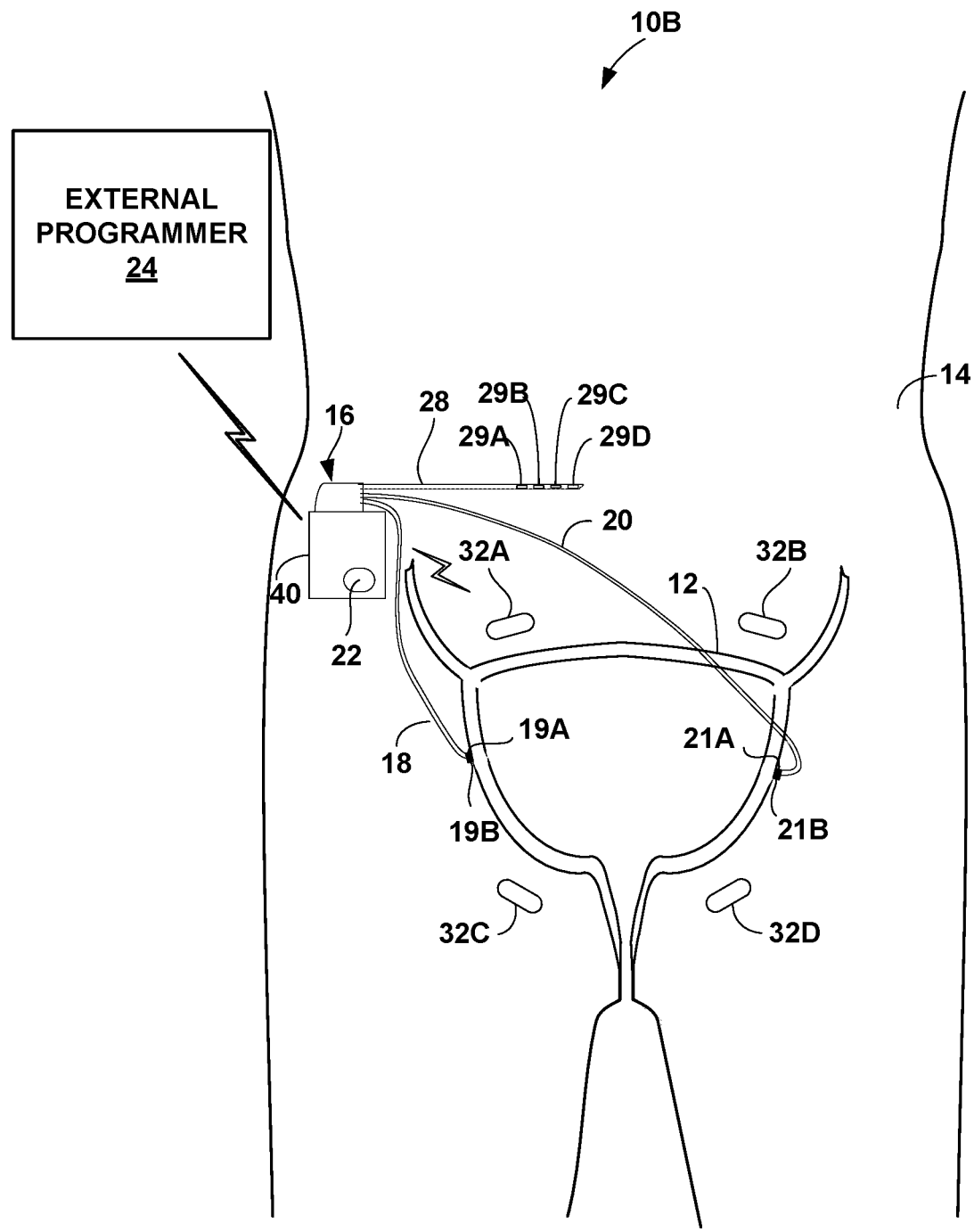
FIG. 2 illustrates, diagrammatically, a patient with an example implanted medical device including a therapy delivery circuitry.

FIG. 2 is conceptual diagram illustrating another example therapy system 10B that delivers stimulation therapy to manage, e.g., urinary incontinence or other condition of patient 14. Therapy system 10B includes a distributed array of electrical stimulators, referred to herein as microstimulators 32A-32D (collectively referred to herein as "microstimulators 32"), in addition to IMD 16, leads 18, 20, and 28, sensing circuitry 22, and programmer 24. In other examples, therapy system 10B includes a distributed array of microstimulators 32 instead of one or more of IMD 16, leads 18, 20, and 28, or sensing circuitry 22. Microstimulators 32 may be configured to generate and deliver electrical stimulation therapy to patient 14 via one or more electrodes. Microstimulators 32 have a smaller size than IMD 16, and in some examples may be leadless.

IMD 16 may be configured to deliver electrical stimulation therapy to patient 14 via microstimulators 32. For example, IMD 16 may communicate wirelessly with microstimulators 32 via wireless telemetry to control delivery of electrical stimulation to patient 14 via microstimulators 32. In the example of FIG. 2, microstimulators 32 may be implanted at different target stimulation sites. For example, microstimulators 32A and 32B may be positioned to stimulate a different set of nerves than microstimulators 32C and 324D. As an example, microstimulators 32A and 32B may target sacral nerves, while microstimulators 32C and 32D target the pudendal nerve. In other examples, microstimulators 32 may be implanted at various locations within the pelvic floor region, e.g., at different positions in proximity to the sacrum to target different nerves within the pelvic region. The illustrated number and configuration of microstimulators 32 is merely exemplary. Other configurations, i.e., number and position of microstimulators, are possible.

Systems 10A and 10B shown in FIGS. 1 and 2, respectively, are examples of therapy systems that may each provide reminder electrical stimulation and/or electrical stimulation therapy according to one or more cycle settings to manage urgency and/or urinary incontinence. Systems with other configurations of leads, electrodes, and sensors may also be used to implement the techniques described herein. Additionally, in other examples, a system may include more than one IMD 16.

Figure 3:
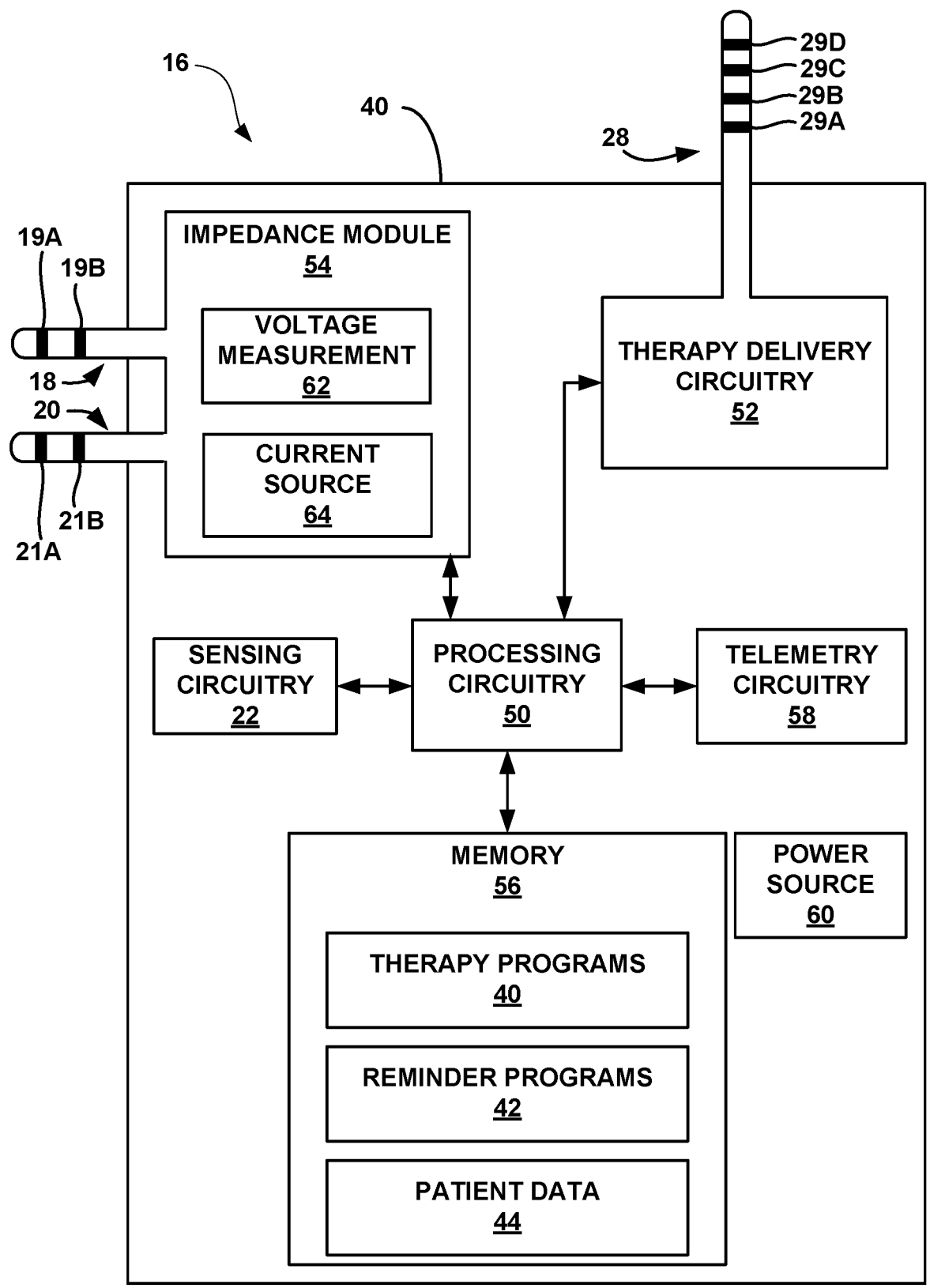
FIG. 3 is a functional block diagram illustrating an example configuration of the implantable medical device of FIGS. 1 and 2.

FIG. 3 is a functional block diagram of an example configuration of IMD 16. In the illustrated example, IMD 16 includes sensing circuitry 22, processing circuitry 50, therapy delivery circuitry 52, impedance module 54, memory 56, telemetry circuitry 58, and power source 60. In various examples, processing circuitry 50, as well as other processing circuitry described herein, can include any one or more microprocessors, digital signal processors (DSPs), application specific integrated circuits (ASICs), field programmable gate arrays (FPGAs), or any other equivalent integrated or discrete logic circuitry, as well as any combinations of such components. The functions attributed to processing circuitry 50, as well as other processing circuitry described herein, herein may be embodied as hardware, firmware, software or any combination thereof.

In the example of FIG. 3, under the control of processing circuitry 50, therapy delivery circuitry 52 (which may also be referred to as a therapy delivery module) is configured to generate and deliver electrical stimulation via selected electrodes 29 of lead 28, alone or in combination with electrodes of another lead or of a housing 30 of IMD 16. For example, processing circuitry 50 may control therapy delivery circuitry 52 by accessing memory 56 to selectively access and load one or more therapy programs or reminder programs into therapy delivery circuitry 52. Therapy delivery circuitry 52 may include stimulation generation circuitry configured to generate and deliver electrical stimulation according to the one or more cycle settings or reminder therapy programs. Therapy delivery circuitry 52 may also be referred to as a stimulation generator.

In some examples, therapy delivery circuitry 52 generates therapy in the form of electrical pulses. In such examples, relevant stimulation parameters for a therapy program may include a voltage amplitude, a current amplitude, a frequency (e.g., pulse rate), a pulse width, a duty cycle, or the combination of electrodes 29 with which therapy delivery circuitry 52 delivers the electrical stimulation signals to tissue of patient 14. In other examples, therapy delivery circuitry 52 may generate electrical stimulation in the form of continuous waveforms. In such examples, relevant stimulation parameters for a therapy program may include a voltage amplitude, a current amplitude, a frequency, a shape of the stimulation signal, a duty cycle of the stimulation signal, or the combination of electrodes 30, 32 with which therapy delivery circuitry 52 delivers the electrical stimulation signals to tissue of patient 12.

In some examples, patient 14 may provide patient input to IMD 16 using programmer 24 or another device, or directly via IMD 16. For example, patient 14 may provide patient input to IMD 16 using sensing circuitry 22 when sensing circuitry 22 includes a motion sensor that is responsive to tapping (e.g., by patient 14) on skin superior to IMD 16. When sensing circuitry 22 includes a motion sensor that is responsive to tapping, upon detecting the pattern of tapping that indicates a particular patient input, processing circuitry 50 may determine that the patient input was received. The number, rate, or pattern of taps may be associated in memory 56 with the different programming capabilities. In this way, patient 14 may directly control the delivery of therapy by IMD 16 in the event that programmer 24 is not within reach of patient 14.

Regardless of whether patient input is received from programmer 24 or other device, the patient input may indicate an urge felt by patient 14, a leakage incident experienced by patient 14, an imminent voiding event predicted by patient 14, a voluntary voiding event undertaken by patient 14 or other information that may affect the timing or intensity level of electrical stimulation delivered by IMD 16. Throughout the disclosure, the term "intensity" is used to describe a level of electrical stimulation delivered to a patient. An intensity of stimulation may be a function of, for example, a current or voltage amplitude of the stimulation signal generated and delivered by IMD 16, the frequency of the stimulation signal, the shape of the stimulation signal, the duty cycle of the stimulation signal, the electrode combination used to deliver the stimulation signal, or any combination of the stimulation parameters. Thus, in some examples, intensity of stimulation may be modulated by modifying an amplitude of the electrical stimulation applied to the patient. Amplitude of electrical stimulation may refer to a magnitude of the voltage and/or current of a stimulation signal applied to the patient by IMD 16. For example, IMD 16 may increase/decrease a voltage and/or current delivered to the patient to increase/decrease the intensity of the electrical stimulation.

In the example of FIG. 3, therapy delivery circuitry 52 is electrically coupled to a single lead 28, and therapy delivery circuitry 52 delivers electrical stimulation to a tissue site of patient 14 via selected electrodes 29A-29D carried by lead 28. A proximal end of lead 28 extends from housing 30 of IMD 16, and a distal end of lead 28 extends to one or more target therapy sites, e.g., within a pelvic floor of patient 14. In some examples, target therapy sites may include tissue proximate a sacral nerve, a pudendal nerve, a hypogastric nerve, a urinary sphincter, or a detrusor muscle, although other target therapy sites may be used. In other examples, therapy delivery circuitry 52 may deliver electrical stimulation with electrodes on more than one lead and each of the leads may carry one or more electrodes. The leads may be configured as axial leads with ring electrodes and/or paddle leads with electrode pads arranged in a two-dimensional array. Additionally, or alternatively, the leads may include segmented and/or partial ring electrodes. The electrodes may operate in a bipolar or multi-polar configuration with other electrodes, or may operate in a unipolar configuration referenced to an electrode carried by outer housing 30 of IMD 16. In yet other examples, such as system 10B shown in FIG. 2 that includes microstimulators 32, processing circuitry 50 may act as a "master" module that controls microstimulators 32 to deliver stimulation at target therapy sites. In other examples, however, one of microstimulators 32 may act as a master module or microstimulators 32 may be self-controlled.

In the example of FIG. 3, impedance module 54 includes voltage measurement circuitry 62 and current source 64, and may include an oscillator (not shown) or the like for producing an alternating signal, as is known. In some examples, as described above with respect to FIG. 1, impedance module 54 may use a four-wire, or Kelvin, arrangement. As an example, processing circuitry 50 may periodically control current source 64 to, for example, source an electrical current signal through electrode 19A and sink the electrical current signal through electrode 21A. Impedance module 54 may also include a switching module (not shown) for selectively coupling electrodes 19A, 19B, 21A, and 21B to current source 64 and voltage measurement circuitry 62. Voltage measurement circuitry 62 may measure the voltage between electrodes 19B and 21B. Voltage measurement circuitry 62 may include sample and hold circuitry or other suitable circuitry for measuring voltage amplitudes. Processing circuitry 50 determines an impedance value from the measured voltage values received from voltage measurement circuitry 52.

In examples in which sensing circuitry 22 includes a pressure sensor, processing circuitry 50 may determine a bladder pressure value based on signals received from the pressure sensor. Processing circuitry 50 may determine whether contractions of bladder 12 are indicative an imminent incontinence event, for example, based on comparison of the sensed pressure to a pressure threshold that indicates an imminent event. For example, processing circuitry 50 may detect an imminent incontinence event when the sensed pressure is greater than the pressure threshold.

The threshold values stored in memory 56 may be determined using any suitable technique. In some examples, the threshold values may be determined during implantation of IMD 16 or during a trial period in a clinician's office following the implant procedure. For example, a clinician may record impedance values during involuntary voiding events and use the recorded impedance values or values calculated based on the recorded values as threshold values. These threshold values may be adapted over time based on patient input, e.g., via external programmer 24. As described above, patient 14 may indicate, via programmer 24, when an involuntary voiding event takes place. When the patient input is received, processing circuitry 50 may determine an impedance value during the event or immediately prior to the event based on signals received from impedance module 54. A new threshold value may be determined using this impedance value. For example, the threshold value stored may be a running average of impedance values measured during involuntary voiding events.

In some examples, IMD 16 includes impedance sensing module 54 and not sensing circuitry 22, while in other examples IMD 16 includes sensing circuitry 22 but not impedance sensing module 54. Moreover, in some examples, sensing circuitry 22 and/or impedance sensing module 54 may be physically separate from IMD 16. Physically separate sensors may be useful in examples in which either sensing circuitry 22 and/or impedance sensing module 54 sense one or more physiological parameters at a location that is not accessible by IMD 16 or difficult to access by IMD 16. However, in other examples of IMD 16, IMD 16 may not include impedance module 54 or sensing circuitry 22, and may include other sensing circuitry or may not include any sensing circuitry configured to sense a patient parameter.

Processing circuitry 50 may control therapy delivery circuitry 52 to deliver electrical stimulation therapy based on patient input received via telemetry circuitry 58. Telemetry circuitry 58 includes any suitable hardware, firmware, software or any combination thereof for communicating with another device, such as programmer 24 of systems 10A and 10B. Under the control of processing circuitry 50, telemetry circuitry 58 may receive downlink telemetry, e.g., patient input, from and send uplink telemetry to programmer 24 with the aid of an antenna, which may be internal and/or external. Processing circuitry 50 may provide the data to be uplinked to programmer 24 and the control signals for the telemetry circuit within telemetry circuitry 58, and receive data from telemetry circuitry 58.

Processing circuitry 50 may control telemetry circuitry 58 to exchange information with medical device programmer 24. Processing circuitry 50 may transmit operational information and receive stimulation programs or stimulation parameter adjustments via telemetry circuitry 58. Also, in some examples, IMD 16 may communicate with other implanted devices, such as stimulators, control devices, or sensors, via telemetry circuitry 58.

Memory 56 stores instructions for execution by processing circuitry 50. Memory 56 may store one or more therapy programs for controlling delivery of electrical stimulation therapy by therapy delivery circuitry 52, one or more reminder programs, or both therapy programs and reminder programs. In some examples, memory 56 stores patient parameter information, such as information generated by impedance module 54 and/or sensing circuitry 22. For example, information related to measured impedance and determined posture may be recorded for long-term storage and retrieval by a user, or used by processing circuitry 50 for adjustment of stimulation parameters, such as amplitude, pulse width, and pulse rate. Memory 56 may include separate memories for storing instructions, electrical signal information, stimulation programs, data pertaining to a voiding diary of patient 14, and other data.

In the example shown in FIG. 3, memory 56 stores therapy programs 40, reminder programs 42, and patient data 44. Therapy programs 40 store one or more therapy programs for use by processing circuitry 50 and therapy delivery circuitry 52 to control the delivery of electrical stimulation therapy to patient 14. In some examples, for each stored therapy program, the stored information may include parameters pertaining to the values of time X and time Y of a cycle setting of the therapy program, the electrode combination with which therapy delivery circuitry 52 delivers electrical stimulation to patient 14, and the electrical stimulation parameter values defining the electrical stimulation signal delivered to patient 14.

In some examples, it may be efficacious for IMD 16 to deliver electrical stimulation therapy according to a plurality of cycle settings over time. For example, IMD 16 may deliver electrical stimulation therapy according to a first cycle setting for a first period of time (a first cycle time period), and subsequently deliver electrical stimulation therapy according to one or more different cycle settings for additional respective periods of time. Thus, therapy programs 40 may store multiple cycle settings that can be selected by processing circuitry 50. As discussed in further detail below, processing circuitry 50 may select the cycle setting by, for example, selecting a therapy program, which may include a cycle setting as part of its parameters, or by selecting a stored cycle setting, which can be stored in memory 56. In some examples, memory 56 may store a list of cycle settings in a predetermined order, and processing circuitry 50 may select cycle settings from the list in the predetermined order. Thus, at the end of a cycle time period or at another suitable time, processing circuitry 50 may select a next cycle setting to use to control delivery of electrical stimulation by therapy delivery circuitry 52 by selecting the next cycle setting in the preordered list.

In other examples, memory 56 may store a list of cycle settings, and processing circuitry 50 may pseudo-randomly select cycle settings from the list, e.g., using a pseudo random counter, each number in the counter being associated with a stored cycle setting, or using any other suitable means. Thus, at the end of a cycle time period or at another suitable time, processing circuitry 50 may select a next cycle setting to use to control delivery of electrical stimulation by therapy delivery circuitry 52 by pseudo-randomly select cycle settings from a predetermined list of cycle settings.

Reminder programs 42 may include parameters pertaining to the timing, intensity, and duration of the electrical reminder therapy to be delivered to patient 14. Reminder therapy may be delivered to patient 14 as a reminder for patient 14 to voluntarily void, or as a reminder of the existence of therapy.

Patient data 44 may include, for example, a voiding diary (discussed in further detail below), physiological parameter values sensed by sensing circuitry 22, impedance module 54, or both, and any other suitable patient data 44.

In some examples, the stimulation parameter values of a therapy program stored by memory 56 may define a therapy with an intensity below a motor and/or perception threshold of the target tissue being stimulated. For example, the electrical stimulation may have an intensity below a motor threshold such that the electrical stimulation delivered by IMD 16 does not result in a motor response from the patient. A motor response may be reported by the patient, observed by a clinician, or automatically detected by one or more sensors internal or external to the patient. An example of motor response can be, for example, an acute motor response, e.g., muscle twitch, induced by the electrical stimulation. When stimulating one of a spinal nerve, sacral nerve, pudendal nerve, or the like, the physiological response may be a contraction of a toe of the patient, a flexing of an anal sphincter of the patient, or a detected signal on an EMG.

As another example, the electrical stimulation delivered by IMD 16 may have an intensity below a perception threshold such that the stimulation is not perceived by patient 14. A stimulation perception response may be observed and reported by the patient, e.g., as a sensation induced by the electrical stimulation therapy. In some examples, perception of the stimulation by patient 14 may occur prior to an observed response of a muscle that is being driven by the nerve being stimulated. In other words, the perception of the stimulation by the patient may occur at a lower threshold than the motor threshold.

For examples in which the stimulation parameter values a therapy program define a therapy with an intensity below a motor and/or perception threshold of the target tissue being stimulated, it may be desirable to gradually increase the intensity of the stimulation at the beginning of the delivery of therapy, or gradually decrease the intensity of the stimulation at the end of the delivery of therapy, until the desired intensity is reached. A gradual increase or decrease in the intensity of stimulation may be known as "ramping on" or "ramping off" the stimulation, respectively, and may help ensure that stimulation does not result in a motor evoked potential or in the perception of electrical stimulation by patient 14, where such results are to be avoided.

Memory 56 may include any volatile, non-volatile, magnetic, or electrical media, such as a random access memory (RAM), read-only memory (ROM), non-volatile RAM (NVRAM), electrically-erasable programmable ROM (EEPROM), flash memory, and the like. Memory 56 may store program instructions that, when executed by processing circuitry 50, cause IMD 16 to perform the functions ascribed to IMD 16 herein.

Power source 60 delivers operating power to the components of IMD 16. Power source 60 may include a battery and a power generation circuit to produce the operating power. In some examples, the battery may be rechargeable to allow extended operation. Recharging may be accomplished through proximal inductive interaction between an external charger and an inductive charging coil within IMD 16. In other examples, an external inductive power supply may transcutaneously power IMD 16 whenever stimulation therapy is to occur.

Although processing circuitry 50, therapy delivery circuitry 52, and telemetry circuitry 58 may be separate modules, in some examples, two or more of processing circuitry 50, therapy delivery circuitry 52, and telemetry circuitry 58 can be functionally integrated. In some examples, processing circuitry 50, therapy delivery circuitry 52, and telemetry circuitry 58 correspond to individual hardware units, such as ASICs, DSPs, FPGAs, or other hardware units.

Figure 4:
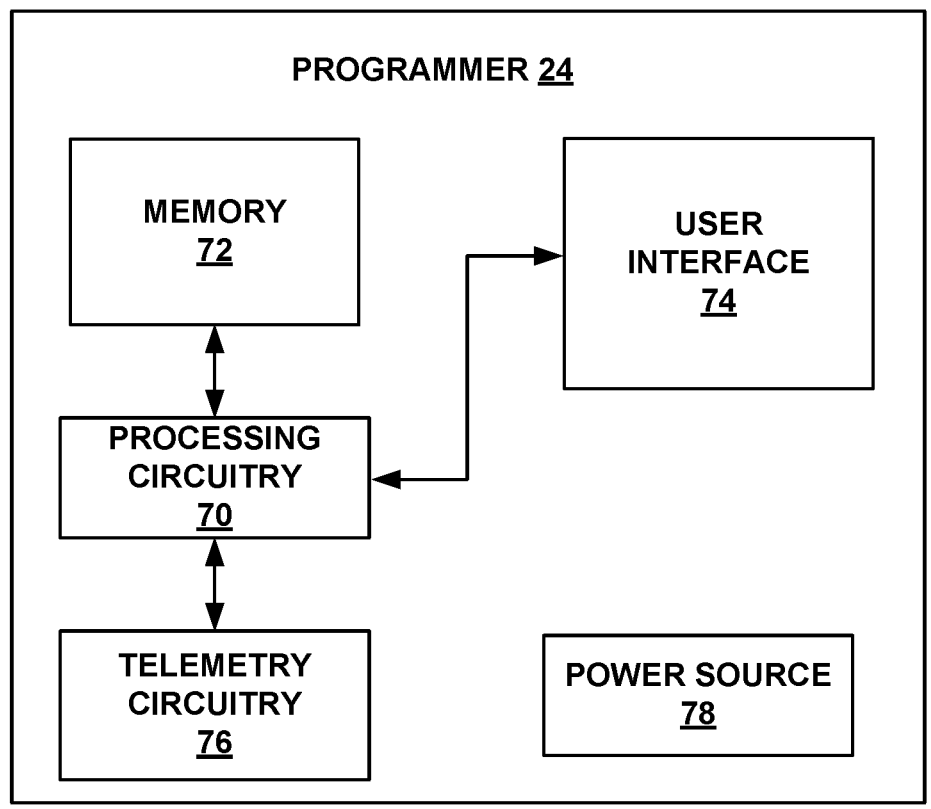
FIG. 4 is a functional block diagram illustrating an example configuration of the external programmer of FIGS. 1 and 2.

FIG. 4 is a functional block diagram illustrating example components of example external programmer 24. While programmer 24 may generally be described as a hand-held computing device, the programmer may be a notebook computer, a cell phone, or a workstation, for example. As illustrated in FIG. 4, external programmer 24 may include a processing circuitry 70, memory 72, user interface 74, telemetry circuitry 76, and power source 78. Memory 72 may store program instructions that, when executed by processing circuitry 70, cause processing circuitry 70 to provide the functionality ascribed to programmer 24 throughout this disclosure.

In some examples, memory 72 of programmer 24 may store a plurality of therapy programs defining one or more electrical stimulation parameter values and/or cycle settings for the delivery electrical stimulation therapy, similar to those stored in memory 56 of IMD 16. The therapy programs stored in memory 72 may be downloaded into memory 56 of IMD 16. Memory 72 may also include reminder programs defining one or more parameters for the delivery of electrical reminder stimulation. The reminder programs stored in memory 72 also may be downloaded into memory 56 of IMD 16.

Memory 72 may include any volatile, non-volatile, fixed, removable, magnetic, optical, or electrical media, such as RAM, ROM, CD-ROM, hard disk, removable magnetic disk, memory cards or sticks, NVRAM, EEPROM, flash memory, and the like. Processing circuitry 70 can take the form one or more microprocessors, DSPs, ASICs, FPGAs, programmable logic circuitry, or the like, and the functions attributed to processing circuitry 70 herein may be embodied as hardware, firmware, software or any combination thereof.

User interface 74 may include a button or keypad, lights, a speaker for voice commands, and a display, such as a liquid crystal (LCD). In some examples the display may be a touch screen. As discussed in this disclosure, processing circuitry 70 may present and receive information relating to stimulation therapy via user interface 74. For example, processing circuitry 70 may receive patient input via user interface 74. The patient input may be entered, for example, by pressing a button on a keypad or selecting an icon from a touch screen. Patient input may include, but is not limited to, input that indicates an urge felt by the patient, a leakage incident experienced by the patient, an imminent voiding event predicted by the patient, or a voluntary voiding event to be undertaken by the patient.

Telemetry circuitry 76 supports wireless communication between IMD 16 and external programmer 24 under the control of processing circuitry 70. Telemetry circuitry 76 may be substantially similar to telemetry circuitry 58 described above, providing wireless communication via an RF or proximal inductive medium. In some examples, telemetry circuitry 76 may include an antenna, which may take on a variety of forms, such as an internal or external antenna. An external antenna that is coupled to programmer 24 may correspond to a programming head that may be placed over IMD 16. Telemetry circuitry 76 may also be configured to communicate with another computing device via wireless communication techniques, or direct communication through a wired connection. Examples of local wireless communication techniques that may be employed to facilitate communication between programmer 24 and another computing device include RF communication according to IEEE 802.11 or Bluetooth specification sets, infrared communication, e.g., according to an IrDA standard, or other standard or proprietary telemetry protocols. In this manner, other external devices may be capable of communicating with programmer 24 without needing to establish a secure wireless connection.

Power source 78 delivers operating power to the components of programmer 24. In some examples, power source 78 may include a battery, such as a rechargeable or non-rechargeable battery. A non-rechargeable battery may be selected to last for several years, while a rechargeable battery may be inductively charged from an external device, e.g., on a daily or weekly basis. Recharging of a rechargeable battery may be accomplished by using an alternating current (AC) outlet or through proximal inductive interaction between an external charger and an inductive charging coil within programmer 24

Patient 14 may also interact with user interface 74 of programmer 24 to store data pertaining to voiding events in memory 72 of programmer 24 or memory 56 of IMD 16. In this manner, patient 14 may create a voiding diary that contains data indicating, for example, the number, frequency, and timing of involuntary voiding events. For example, patient 14 may enter, via a keypad or touch screen of user interface 74, an indication that an involuntary voiding event occurred at a particular time. Processing circuitry 70 of programmer 24 may correlate the timing of the voiding event with other data, such as the therapy program and/or specific cycle setting being used by IMD 16 at the time of the voiding events to deliver electrical stimulation therapy, patient posture data, patient activity data, and bladder impedance data sensed by impedance module 54 and sensing circuitry 22 at or shortly before the time of the voiding event.

Correlating involuntary voiding events with a particular therapy program or a particular cycle setting (multiple therapy programs may have the same cycle setting) may help control the timing with which processing circuitry 50 or 70 changes a currently implemented cycle setting. For example, processing circuitry 50 or 70 may compare the number of involuntary voiding events associated with a particular therapy program or a particular cycle setting with a predetermined threshold value (which may be stored in memory 56 or memory 72), and, in response to determining the number of involuntary voiding events is greater than or equal to the threshold value, processing circuitry 50 or 70 may control therapy delivery circuitry 52 to deliver therapy according to a different cycle setting. For example, as discussed below, the different cycle setting may be selected as the next cycle setting in a predetermined order of a plurality of cycle settings, or may be pseudo-randomly selected from a list of predetermined cycle settings.

In other examples, patient 14 may also interact with user interface 74 to cause memory 72 to store data pertaining to a voluntary voiding event or an increased urge event, which processing circuitry 70 may correlate with other data sensed by impedance module 54 or sensing circuitry 22 at the time of the voluntary voiding event or increased urge event. In other examples, processing circuitry 70 of programmer 24 may transmit the data regarding the patient input indicative of the occurrence of one or more voiding events to IMD 16, and processing circuitry 50 of IMD 16 may perform any of the functions described herein instead of processing circuitry 70.

In other examples, processing circuitry 50 may independently cause memory 56 of IMD 16 to store data pertaining to various urinary events, which may be sensed by IMD 16 (e.g., by sensing circuitry 22) or indicated by patient requests to deliver or suspend stimulation, which, as described above, may occur when patient 14 senses that an involuntary voiding episode may be imminent. In such examples, processing circuitry 50 may cause the data to be stored in the voiding diary as a record of the number, frequency, and timing of various urinary events, and, in some cases, as one or more physiological parameters sensed by sensing circuitry 22 or another sensing device. As with voiding data manually entered by patient 14 into programmer 24, processing circuitry 50 of IMD 16 may correlate the timing of a request for extra stimulation with other data, such as patient posture data, patient activity data, and bladder impedance data sensed by impedance module 54 and sensing circuitry 22 at or around the time of the event. Thus, a voiding diary of patient 14 may contain data entered by patient 14 and data independently stored by processing circuitry 50 and memory 56 of IMD 16, thereby providing a more robust representation of symptoms experienced by patient 14 than would be provided by patient-entered data or data independently stored by IMD 16 alone.

FIGS. 5-11 are flow diagrams illustrating various techniques related to controlling delivery of electrical stimulation therapy to a patient according to one or more cycle settings, e.g., to help manage an incontinence condition of the patient. As described herein, the techniques illustrated in FIGS. 5-11 may be employed using one or more components of systems 10A and 10B, which have been described above with respect to FIGS. 1-4. Although described as being performed by IMD 16 of system 10A (FIG. 1), in other examples, the techniques of FIGS. 5-11 may be performed, in whole or in part, by processing circuitry and memory of other devices of a medical device system, alone or in combination with processing circuitry 50 of IMD 16. Further, although the example technique of FIG. 5 may be implemented by either system 10A of FIG. 1 or system 10B of FIG. 2, other systems and devices employing the technique of FIG. 5 also may be used in other examples.

Figure 5:
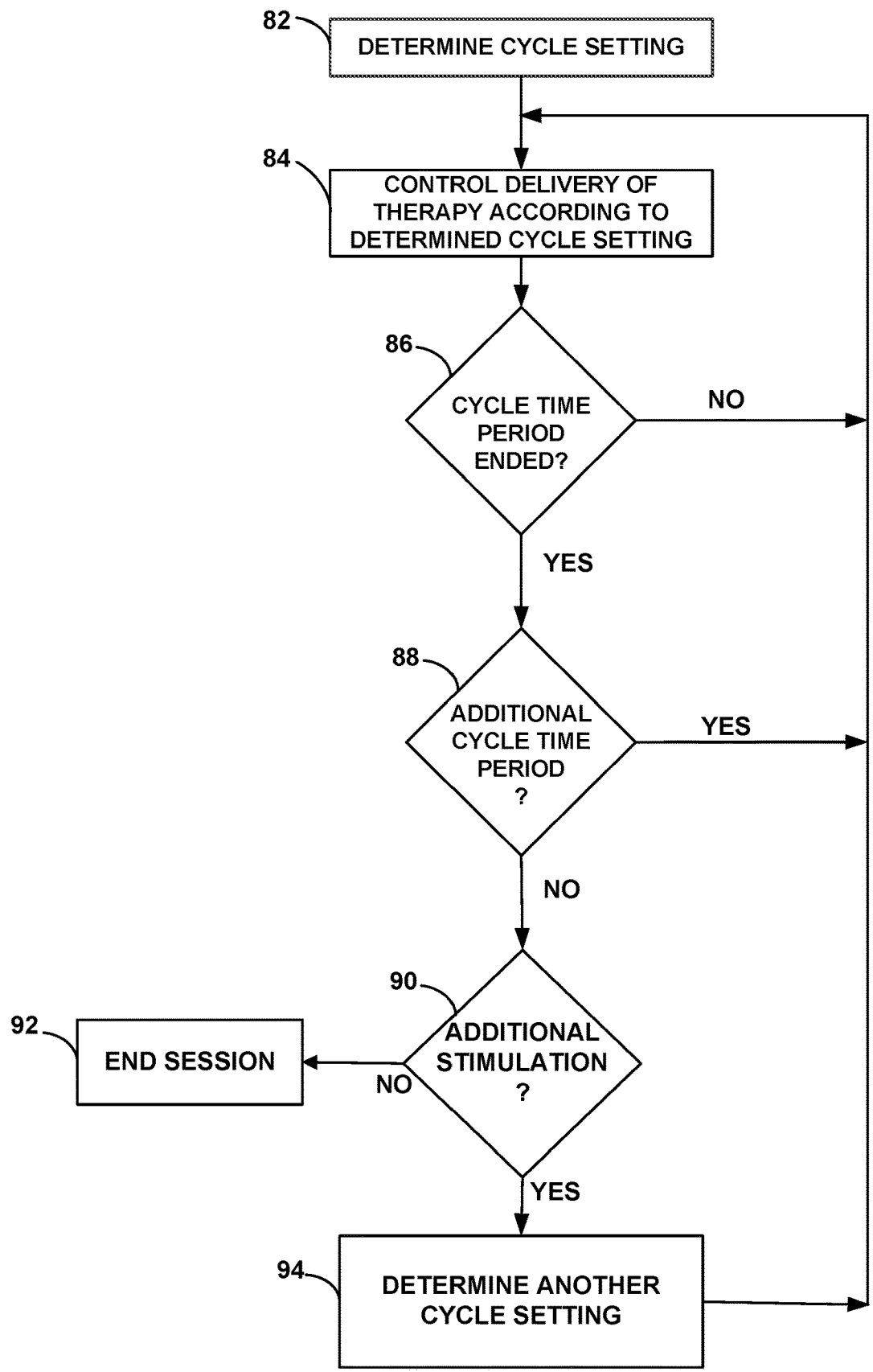
FIG. 5 is a flow diagram illustrating an example technique for delivering electrical stimulation to a patient to manage a patient condition.

FIG. 5 is a flow diagram illustrating an example technique for delivering electrical stimulation to patient 14 according to one or more cycle settings to manage a patient condition, such as, e.g., urinary incontinence. For example, electrical stimulation therapy delivered to patient 14 using the technique shown in FIG. 5 may help reduce symptoms of an incontinence condition of patient 14. In some examples, the technique of FIG. 5 may be implemented as a set of instructions executable by processing circuitry 50 and stored by memory 56 of IMD 16 or a memory of another device.

As shown in FIG. 5, processing circuitry 50 of IMD 16 may determine a cycle setting (referred to herein as a "first cycle setting") by which to deliver electrical stimulation to patient 14, e.g., for treatment of urinary incontinence or another condition (82). In some examples, processing circuitry 50 may determine the first cycle setting by receiving the cycle setting from another device, such as programmer 24 via the respective telemetry circuitries 58,76. In other examples, processing circuitry 50 may determine the first cycle setting by retrieving a stored cycle setting from memory 56 of IMD 16.

Processing circuitry 50 may determine the first cycle setting (82) using any suitable technique. In some examples, processing circuitry 50 may determine the first cycle setting by selecting the first cycle setting from a list of a plurality of cycle settings stored by memory 56 (or a memory of another device). For example, memory 56 may store the list in a predetermined order, and processing circuitry 50 may select cycle settings from the list in the predetermined order. Thus, in some examples, in order to determine the first cycle setting (82), processing circuitry 50 may select the first cycle setting in the list, select any cycle setting in the list as a starting point for selecting the cycle settings in the predetermined order, or select the next cycle setting in the list if another cycle setting from the list has previously been used. As another example, processing circuitry 50 may pseudo-randomly select cycle settings from the plurality of stored cycle settings. Thus, in some examples, in order to determine the first cycle setting (82), processing circuitry 50 may pseudo-randomly select the first cycle setting from a plurality of predetermined cycle settings, e.g., stored in memory 56. Processing circuitry 50 may be configured to make the pseudo-random selection using any suitable technique, such as by using a pseudo-random number generator that outputs a number that corresponds to a cycle setting in the list of stored cycle settings.

Figure 10:
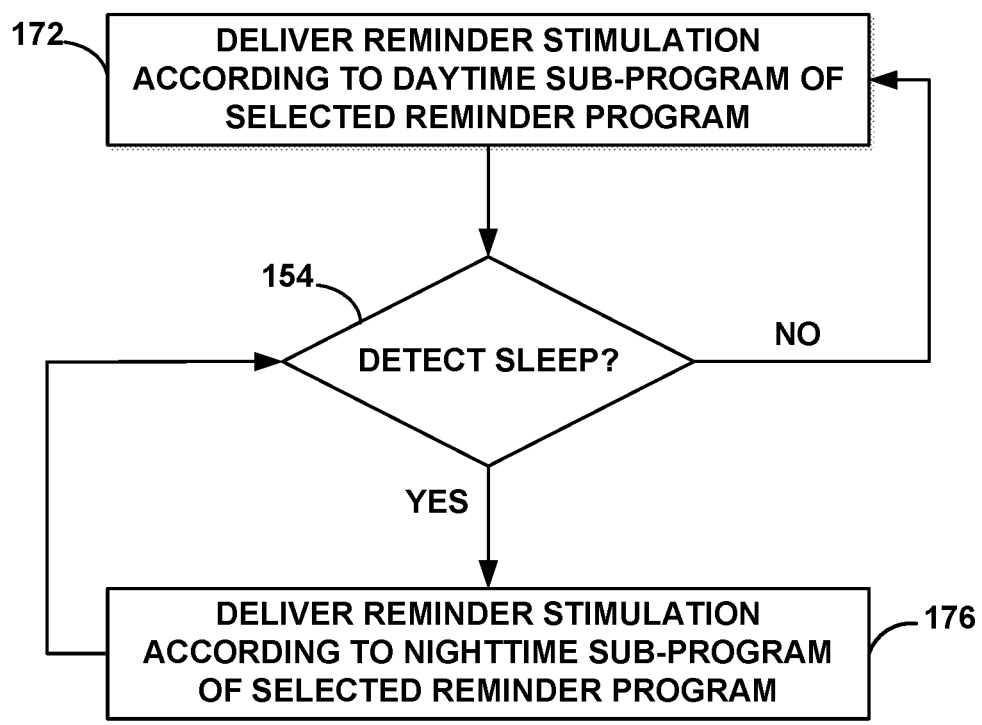
FIG. 10 is a flow diagram illustrating an example technique for delivering reminder therapy to a patient based on a sleep status of the patient.

In other examples, processing circuitry 50 may determine the first cycle setting based on patient data, as described in further detail with respect to FIG. 10.

In the examples described herein in which processing circuitry 50 determines (e.g., selects) a cycle setting, processing circuitry 50 may select the parameter values for the cycle setting itself (e.g., time X and time Y defining a therapy cycle of the cycle setting), or may select a therapy program from stored therapy programs 40 in memory 56 (or a memory of another device). In examples in which processing circuitry 50 determines a cycle setting by selecting a therapy program, processing circuitry 50 may determine the first cycle setting by selecting the first cycle setting from a list of a plurality of cycle settings stored by memory 56 (or a memory of another device) using any suitable technique, including the techniques described above with respect to the selection of a cycle setting from a list of a plurality of stored cycle settings.

After determining the first cycle setting (82), processing circuitry 50 may control therapy delivery circuitry 52 to generate and deliver electrical stimulation therapy to patient 14 based on the determined one or more cycle settings for a first cycle time period. Thus, IMD 16 may deliver electrical stimulation therapy to patient 14 according to the first cycle setting, in which the stimulation is turned on for a predetermined period of time and turned off for a predetermined period of time over the first cycle time period. For example, a cycle setting may cause IMD 16 to deliver the electrical stimulation by repeatedly turning the electrical stimulation on for 16 seconds and off for 8 seconds, over the first cycle time period (e.g., 28 days). In other examples, IMD 16 may repeatedly turn on electrical stimulation for 10 minutes and off for 10 minutes, or on for 30 minutes and off for 23.5 hours, over the first cycle time period. In other examples, IMD 16 may continuously deliver electrical stimulation during the first cycle time period. While four particular cycle settings, i.e., continuous on, 10 minutes on/10 minutes off, 16 seconds on/8 seconds off, and 30 minutes on/23.5 hours off are described, it is understood that other cycle settings and cycle time periods associated with delivery of the electrical stimulation may also be utilized.

In some examples, the first cycle time period, which may be on the order of days or even weeks, may be stored by memory 56 and may be the same for all cycle settings or may differ based on the cycle setting. In the latter example, memory 56 may associate a particular cycle time period with respective cycle settings in memory 56. For example, a first cycle setting may be associated with a first cycle time period of 28 days in memory 56, and a second cycle setting may be associated with a second cycle time period of 21 days in memory 56. In some examples, two or more cycle settings may be associated with the same cycle time period, or all of the stored cycle settings may be associated with different cycle settings.

In the example shown in FIG. 5, after controlling therapy delivery circuitry 52 to generate and deliver electrical stimulation therapy to patient 14 according to the first cycle setting (and other therapy parameter values, which may be defined by a selected therapy program that includes the first cycle setting), processing circuitry 50 may determine whether the first cycle time period has expired (86), e.g., using a timer as shown in FIG. 5. In response to determining the cycle time period has not expired ("NO" branch of block 86), processing circuitry 50 continues to control therapy delivery circuitry 52 to generate and deliver electrical stimulation therapy to patient 14 according to the first cycle setting (84). In response to determining the cycle time period has not expired ("YES" branch of block 86), processing circuitry 50 may determine whether to cause IMD 16 to deliver the electrical stimulation according to the same cycle setting for an additional cycle time period (88). The additional cycle time period may be the same as the first cycle time period or may be different (e.g., longer or shorter than the first cycle time period).

In some examples, processing circuitry 50 may use the same cycle setting for one or more sequential cycle time periods. For example, processing circuitry 50 may determine, e.g., based on a voiding diary stored by memory 56, that the current cycle setting is relatively efficacious for patient 14. As an example, processing circuitry 50 may determine that the number of involuntary voiding events associated with the current cycle setting is less than or equal to a predetermined threshold value, thereby indicating that the current cycle setting is relatively efficacious for patient 14.

In response to determining that electrical stimulation is to be delivered for an additional cycle time period using the same cycle setting ("YES" branch of block 88), processing circuitry 50 controls therapy delivery circuitry 52 to generate and deliver the electrical stimulation to patient 14 according to the first cycle setting (84) for an additional first cycle time period. In response to determining that electrical stimulation is not to be delivered using the same cycle setting, processing circuitry 50 determines whether electrical stimulation is to be subsequently delivered using other cycle (88). For example, processing circuitry 50 may determine whether it has received a signal from programmer 24 indicating therapy delivery should be stopped, or processing circuitry 50 may be configured to deliver electrical stimulation therapy to patient 14 according to only the first cycle setting, e.g., during a trial procedure in which multiple cycle settings are being tested on patient 14.

In response to determining no additional electrical stimulation is to be delivered ("NO" branch of block 90), processing circuitry 50 may end the stimulation session (92). For example, processing circuitry 50 may control therapy delivery circuitry 52 to stop the delivery of any further electrical stimulation to patient 14 or to revert to a different therapy delivery regimen (e.g., delivery of electrical stimulation only in response to patient input or certain detected physiological events, such as a bladder contraction frequency greater than or equal to a threshold value).

In response to determining additional electrical stimulation is to be delivered ("YES" branch of block 90), processing circuitry 50 adjusts the cycle setting accordingly. In the example shown in FIG. 5, processing circuitry 50 determines another cycle setting (94), e.g., using any of the technique described above with respect to selecting a cycle setting (92). For example, at the end of cycle time period or at another suitable time, processing circuitry 50 may select a next cycle setting to use to control delivery of electrical stimulation by therapy delivery circuitry 52 by selecting the next cycle setting in a preordered list of cycle settings stored by memory 56 or by pseudo-randomly selecting another cycle setting from a list of predetermined cycle settings stored by memory 56. Processing circuitry 50 may then control therapy delivery circuitry 52 to stop delivery of electrical stimulation according to the first cycle setting, and to generate and deliver the electrical stimulation according to the adjusted cycle setting (84). Then, the process may be repeated using the determined cycle setting, i.e., IMD 16 may deliver electrical stimulation therapy according to the adjusted cycle setting for one or more cycle time periods. In examples in which processing circuitry 50 determines more than one cycle setting (82, 94), processing circuitry 50 may control therapy delivery circuitry 52 to deliver electrical stimulation therapy to patient 14 according to each of the one or more cycle settings during a corresponding cycle time period.

In other examples of the technique shown in FIG. 5, processing circuitry 50 may not determine whether to continue controlling therapy delivery circuitry 52 to generate and deliver electrical stimulation therapy according to the same cycle setting (88) or determine whether additional electrical stimulation should be delivered (90). Instead, after determining the first cycle period has expired ("YES" branch of block 86), processing circuitry 50 may determine another cycle setting (e.g., by selecting a next cycle setting in a stored ordered list or pseudo-randomly selecting a cycle setting from a plurality of predetermined cycle settings). Processing circuitry 50 may then control therapy delivery circuitry 52 to generate and deliver electrical stimulation therapy to patient 14 according to the determined cycle setting (84).

As described above, the delivery of electrical stimulation therapy to patient 14 by IMD 16, according to of two or more cycle settings for respective predetermined cycle time periods may help to reduce the number of incontinence episodes that patient 14 may experience during a given period of time. In some examples, a patient may become accustomed to the delivery of electrical stimulation, which may result in a return of symptoms or in an otherwise-reduced effectiveness of the electrical stimulation therapy over time. The adaptation response to electrical stimulation may be reduced or avoided by periodically varying one or more parameters of the delivered electrical stimulation, such that stimulation is not delivered to patient 14 according to the same parameters for a relatively long period of time. For example, delivering electrical stimulation to patient 14 according to a combination of different cycle settings over the course of a plurality of cycle time periods may help minimize patient adaptation to the electrical stimulation, and may minimize muscle fatigue that may result from the electrical stimulation. Thus, by selecting a different cycle setting by which IMD 16 delivers electrical stimulation therapy to patient 14 at the expiration of a cycle time period, a recurrence of patient 14's symptoms due to the adaptation phenomenon may be reduced or avoided.

In some examples, IMD 16 may deliver electrical stimulation therapy to patient according to a combination of any number of the available (e.g., stored) cycling settings, each of which may be delivered over one or more cycle time periods, such as 28 days for example, and in any specific sequential order. As an example, IMD 16 may deliver electrical stimulation therapy according to one of the first and second cycle settings at a time for respective (and, in some examples, sequential) cycle time periods, e.g., two 28-day time periods. For example, processing circuitry 50 may control therapy delivery circuitry 52 to deliver electrical stimulation according to a first cycle setting for a first cycle time period, e.g., on for 10 minutes and turned off for 10 minutes over a predetermined period of time, such as one or more 28 day cycle time periods. Subsequent to the first cycle time period expiring, processing circuitry 50 may control therapy delivery circuitry 52 to deliver electrical stimulation is turned according to a second cycle setting for a predetermined second cycle time period. In one example, the second cycle setting defines parameter values that result in electrical stimulation being turned on for 30 minutes (X) and turned off for 23.5 hours (Y) over the second cycle time period, such as one or more 28-day cycle time periods.

As another example, IMD 16 may deliver electrical stimulation therapy according to both the first and second cycle settings for four cycle time periods. i.e., four 28-day time periods. In another example, the first and second cycle settings may be repeated over subsequent cycle time periods. In still another example, the first cycle setting may correspond to the electrical stimulation being turned on for 30 minutes and turned off for 23.5 hours over one or more cycle time periods, and the second cycle setting may correspond to the electrical stimulation being turned on for 10 minutes and turned off for 10 minutes over one or more cycle time periods.

In some examples, IMD 16 may deliver of electrical stimulation therapy to patient 14 according to a combination of different cycle settings during the course of a cycle time period, such as two or more cycle settings out of the four cycle settings described above, i.e., continuous on, 10 minutes on/10 minutes off, 16 seconds on/16 seconds off and 30 minutes on/23.5 hours off. In any such examples in which IMD 16 delivers electrical stimulation therapy to patient 14 according to two or more cycle settings, the sequence in the cycle settings are applied may differ. For example, IMD 16 may initially deliver electrical stimulation therapy to patient 14 by turning stimulation on for 30 minutes and off for 23.5 hours over one or more cycle time periods, followed by either of the other two cycle settings. In another example, IMD 16 may deliver electrical stimulation by turning stimulation on for 16 seconds and off for 8 seconds over one or more cycle time periods, followed by either of the other two cycle settings, and so forth.

Various factors may affect the specific cycle settings by which IMD 16 delivers electrical stimulation therapy to patient 14. In one example, the value of the time period associated with the stimulation being turned on (i.e., time X) and the value of the time period associated with the electrical stimulation being turned off (i.e., time Y) are chosen, e.g., by a clinician or programmer 24, so that time X is selected to generating a desired physiological response from the patient, such as urinary sphincter contraction or a reduction in bladder contraction frequency. In other examples, time X may be selected to achieving a desired patient sensation of the electrical stimulation, or may be based on an expected urge length. In addition, in other examples, such as when the electrical stimulation therapy delivered by IMD 16 is configured to help aid voluntary voiding by patient 14 (e.g., to manage a urinary retention disorder), time X can be selected to achieve a physiological response related to voiding, e.g., a bladder contraction or an urge to void.

In some examples, time Y is linked to a bladder fill time of the patient, which may be determined based on input received from sensing circuitry 22, as described below with respect to FIG. 6. In other examples, time Y is based on patient input, or may be determined based on a typical value for a bladder fill time, such as three hours for example. In addition to or instead of the other examples of time Y, time Y may be determined based on the washout period of the on-cycle, where the washout period may be the period of time over which the therapeutic effects of the electrical stimulation therapy dissipate. The washout period may be determined, for example, as the duration of time between the end of time X and the time at which one or more symptoms of the patient condition have returned (e.g., an incontinence event, an unwanted sensation of urgency by patient 14, a bladder contraction frequency greater than or equal to a stored threshold, and the like).

In another example, processing circuitry 50 may select a therapy program (e.g., the values of time X and time Y of a cycle setting, and the values of the amplitude, frequency or pulse width of the delivered electrical stimulation signal) such that patient 14 perceives the delivery of electrical stimulation therapy by IMD 16. In such examples, IMD 16 may deliver reminder electrical stimulation to patient 14 at an amplitude, frequency, or pulse width that is above the perception threshold of patient 14, thereby causing patient 14 to perceive the electrical stimulation, and reminding patient 14 that electrical stimulation is being delivered or that patient 14 may need to void. In some examples, the reminder stimulation delivered to patient 14 by IMD 16 may include one or more pulses. In other examples, the reminder stimulation may include a continuous waveform signal. In some examples, IMD 16 may deliver electrical reminder stimulation to patient 14 at predetermined intervals, such as once per hour, once every 90 minutes, or at any other suitable interval. For example, a predetermined voiding-reminder interval may generally be between five minutes and three hours, although other voiding-reminder intervals may also be used. In other examples, one or more voiding-reminder intervals may be determined based on the specific needs of patient 14, based on one or more of a determined typical value for bladder fill time Y of patient 14, based on a sleep status of patient 14, or based on other factors such as patient preference.

In some examples, IMD 16 may deliver electrical stimulation therapy and reminder stimulation to patient 14 concurrently, according to one of therapy programs 40 and one of reminder programs 42. That is, the delivery of electrical stimulation therapy and reminder electrical stimulation by IMD 16 to patient 14 may be interleaved. For example, electrical stimulation may be delivered according to a first cycle setting of one of therapy programs 40, e.g., in which electrical stimulation therapy is turned on for 10 minutes and turned off for 10 minutes, and concurrently according to a reminder program 42, in which electrical stimulation comprising a reminder to void is delivered once every 90 minutes, although other combinations of cycle settings and reminder programs may be used in other examples. In other examples, the electrical stimulation therapy and the electrical reminder stimulation may not be delivered by IMD 16 in an interleaved fashion. For example, IMD 16 may deliver the reminder stimulation according to a circadian rhythm of patient 14; e.g., when the patient 14 is likely to be awake and not when patient 14 is sleeping. However, in other examples, the patient reminders may be provided by the electrical stimulation when patient 14 is sleeping, such as in examples in which patient 14 experiences incontinence symptoms while sleeping.

In another example, processing circuitry 50 may select time X and time Y values based on one or more stored power consumption values, such that the X and Y values are configured to improve battery longevity, thereby prolonging the useful life of IMD 16. For example, memory 56 may associate each of the stored cycle settings or therapy programs with respective power consumption values that were previously determined and indicative of the amount of power required to generate and deliver electrical stimulation therapy to patient 14 according to the respective cycle setting or therapy program. Processing circuitry 56 may then select cycle settings from memory 56 (e.g., block 94 in FIG. 5) based on the associated power consumption values. If, for example, power source 60 of IMD 16 is relatively low, then processing circuitry 56 may select a cycle setting that is associated with a relatively low power consumption value. In some examples, processing circuitry 56 may also send a notification to patient 14 (e.g., via programmer 14 or via another mechanism, such as somatosensory circuitry of IMD 16) that indicates that power source 60 is low, such that a visit to a clinic may be desirable.

In examples in which electrical reminder stimulation is desired, processing circuitry 50 also may select one or more reminder programs based on the relative power consumption of the parameters of the reminder program (e.g., the frequency or amplitude of reminder pulses), such that the one or more reminder programs are configured to improve battery longevity or otherwise minimize power consumption.

As discussed above with respect to reminder cycle parameters, processing circuitry 50 may select X and Y values at least partially based on a circadian rhythm of patient 14. For example, different urge length values (X) may be chosen during times when patient 14 is awake (e.g., day time) than during times when patient 14 is asleep (e.g., night time). In another example, different bladder fill time values (Y) may be chosen during the day time than during the night time. Thus, in some examples, a given cycle setting may include at least one daytime cycle setting and at least one nighttime cycle setting.

In other examples, processing circuitry 50 of IMD 16 may cause the X and/or Y values for one or more cycle settings of a particular group to be modified over time, based on a determined efficacy of the electrical stimulation therapy delivered to patient 14 or based on a disease progression of patient 14. For example, if processing circuitry 50 or another device (e.g., programmer 24 or a remote clinician monitoring device) determines that the number and/or frequency of incontinence episodes experienced by patient 14 is increasing over time, then processing circuitry 50 or the other device may incrementally adjust the X and/or Y values of one or more cycle settings until an improvement in the patient condition (e.g., a decrease in the number and/or frequency of incontinence episodes) is determined by processing circuitry 50 or by the processing circuitry of another device. In some examples, a decrease in the number and/or frequency of incontinence episodes may be determined based on patient input, input received by sensing circuitry 22 (e.g., sensed involuntary voiding events), or any combination thereof.

In some examples, processing circuitry 50 (or another device) may select the increments by which the X and/or Y values of a cycle setting are adjusted according to a predetermined technique. For example, processing circuitry may select one or more increment values stored by a table in memory 56 of IMD 16 or memory 72 of programmer 24, and modify the X and/or Y values of the cycle setting based on the selected one or more increment values.

It is believed that the periodic changing of the cycle settings may help improve the therapeutic outcome of the electrical stimulation therapy, e.g., relative to an example in which one cycle setting is used for an indefinite amount of time. Thus, in the example shown in FIG. 5, the determination of another cycle setting (94), e.g., at the end of a cycle time period associated with the previously used cycle setting, may help improve the therapeutic outcome of the electrical stimulation therapy. In some examples, the parameter values associated with the cycle setting and cycle time period described above may be automatically varied by one or more components of IMD 16 and/or programmer 24 (e.g., at block 94 in FIG. 5) in order to determine another cycle setting (94).

In one example, the X and/or Y values for one or more cycle settings may be randomized, or pseudo-randomized, such as by processing circuitry 50 or processing circuitry 70, and varied accordingly. Where the X and/or Y values are varied according to a pseudo-random pattern, processing circuitry 50 may select the X and Y values according to one or more rules for selecting a next cycle setting. For example, one such rule may require processing circuitry 50 to select a cycle setting that is different from the cycle setting selected for the immediately preceding period, and different from the cycle setting selected immediately following one or more uses of the current cycle setting. In other examples, processing circuitry 50 also may use additional or different rules for creating a pseudo-random pattern of cycle settings. Thus, the parameters associated with the cycle setting and cycle time period may be varied so as to avoid adaptation of patient 14 to the electrical stimulation, and also to retain some features of randomness and/or unpredictability. In another example, the parameters associated with the cycle time period may also be varied, either automatically or in response to patient data, so as to avoid adaptation of patient 14 to the electrical stimulation. As with the parameters associated with the cycle setting, the parameters for the cycle time period may be randomized or pseudo-randomized by processing circuitry 50, and varied accordingly.

In still another example, processing circuitry 50 may automatically vary the amplitude, frequency or pulse width of the electrical stimulation therapy delivered by IMD 16 to patient 14, in order to create patient awareness of the electrical stimulation therapy. In some cases, this may provide one or more benefits to the clinical outcome of patient 14. For example, the extent to which a patient perceives the delivery of electrical stimulation therapy may vary, according to the time on and time off values by which stimulation is delivered. In one example, a relatively higher level of patient perception of the delivery of electrical stimulation therapy may occur when electrical stimulation is turned on for 10 minutes and turned off for 10 minutes over one or more cycle time periods, compared to a relatively lower level of patient perception that may occur when electrical stimulation is continuous. However, it should be noted that amplitude, frequency, and pulse width values that result in higher levels of patient perception may vary between patients and even for the same patient.

In some examples in which processing circuitry 50 or processing circuitry 70 randomly or pseudo-randomly varies the parameters associated with one or more of a cycle setting and a cycle time period, the changes to the electrical stimulation therapy delivered by IMD 16 may be implemented gradually over a period of time, such as over a period of weeks, days, or hours. In some examples, such gradual changes to the parameters of the electrical stimulation therapy delivered by IMD 16 may decrease the extent to which patient 14 perceives the change, and may decrease the time it takes for patient 14 to adjust to the new parameters.

Figure 6:
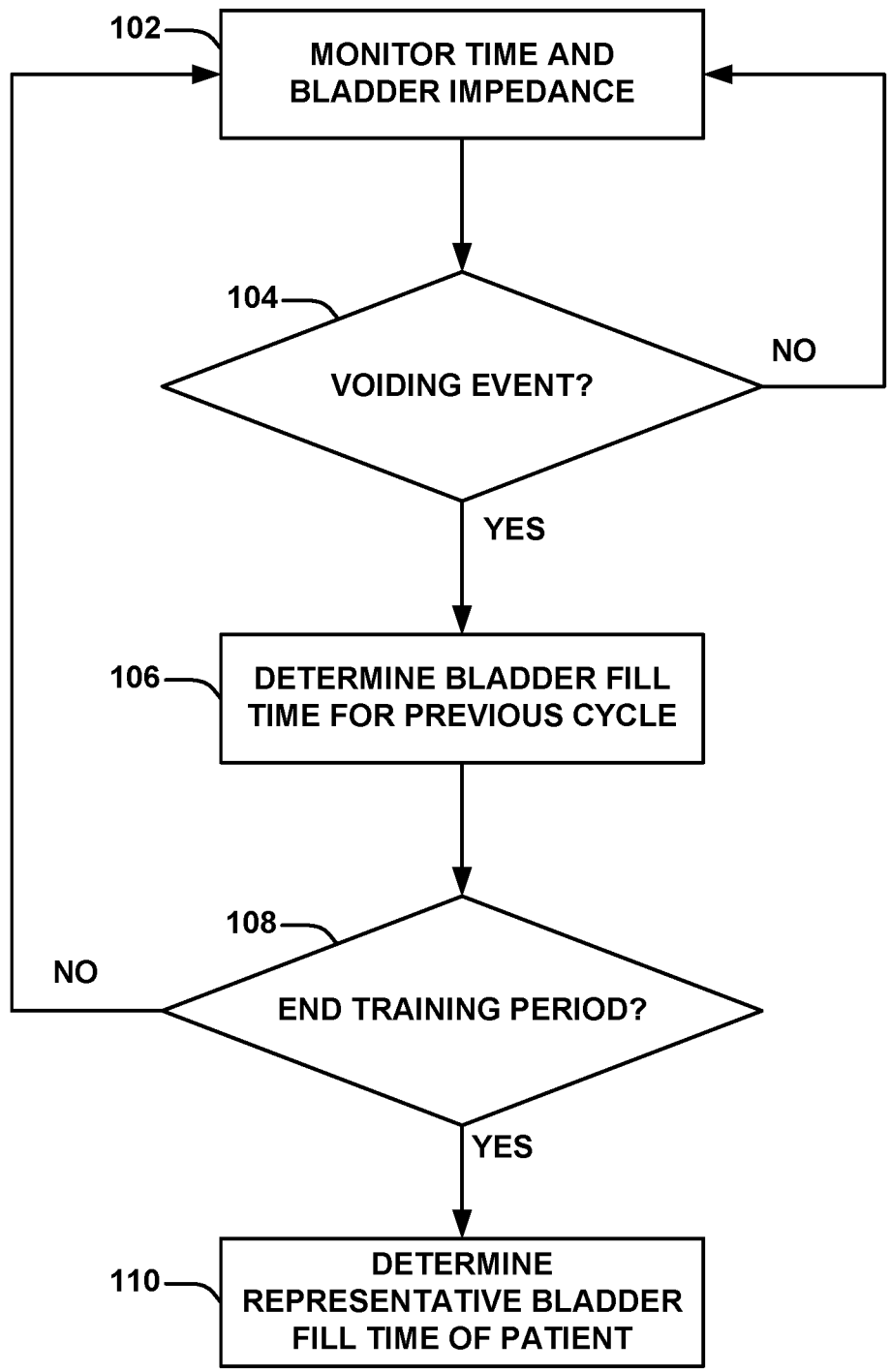
FIG. 6 is a flow diagram illustrating an example technique for determining a representative bladder fill time of a patient and delivering therapy based on the determination.

FIG. 6 is a flow diagram illustrating an example technique for determining a representative bladder fill time of patient 14 in accordance with the example technique of FIG. 5. As described above with respect to FIG. 5, the value of time Y, (i.e., the time during which electrical stimulation is turned off) of a cycle setting may be linked to a bladder fill time of patient 14. In some examples, processing circuitry 50 may determine a value for Y based on patient input, such as an input received by processing circuitry 50 from programmer 24. In other examples, processing circuitry 50 may determine a value for Y based on a typical value for a bladder fill time, such as three hours. However, in some examples, it may be desirable to determine a representative bladder fill time of a patient based on values obtained during a training period for IMD 16.

During a training period for IMD 16, processing circuitry 50 may monitor the bladder impedance and bladder fill time of patient 14 during the course of one or more micturition cycles, and determine a representative bladder fill time of patient 14 to be stored in memory 56. For example, in the example shown in FIG. 6, processing circuitry 50 may monitor the time elapsed since a previous voiding event and the impedance values of bladder 10 received from sensing circuitry 22 (102). In response to determining no voiding event is detected ("NO" branch of block 104), processing circuitry 50 may continue monitoring the bladder impedance and fill time of patient 14. In response to detecting a voiding event of patient 14 ("YES" branch of block 104), processing circuitry 50 determines a bladder fill time for the previous micturition cycle (106). In some examples, the bladder fill time may be the amount of time elapsed between the end of one voiding event and the beginning of the next voiding event. Upon determining the bladder fill time for the previous micturition cycle (106), processing circuitry 50 determines whether to end the training period of IMD 16 (108). Processing circuitry 50 may make this determination based on a predetermined number of fill cycles that have elapsed since the beginning of technique, for example, or based on other considerations, such as a predetermined length of time.

If processing circuitry 50 determines that training period has not ended ("NO" branch of block 108), then the technique returns to (102) to determine a bladder fill time for the next micturition cycle of patient 14. The process (102, 104, 106, 108) may then repeat until processing circuitry 50 determines that the training period has ended ("YES" branch of block 108), at which point processing circuitry 50 may determine a representative bladder fill time of patient 14 based on the bladder fill times determined during the training period (110). In some examples, processing circuitry 50 may determine the representative bladder fill time based on a mean or median value of the bladder fill times, although other algorithms or methods may be used. Processing circuitry 50 then may store the determined representative bladder fill time of patient 14 in memory 56 of IMD 16, which may be accessed by processing circuitry 50 or processing circuitry 70 during the selection of one or more cycle settings at blocks 82 and 94 of FIG. 5. In some examples, processing circuitry 50 automatically updates the Y time of at least one of the stored cycle settings based on the determined bladder fill time. For example, processing circuitry 50 may update the Y time to be less than or equal to the determined bladder fill time, or greater than the bladder fill time. In some examples, the example technique of FIG. 6 may be repeated more than once for patient 14, such as at predetermined intervals, or based on patient data stored in memory 56 during the course of treatment.

Figure 7:
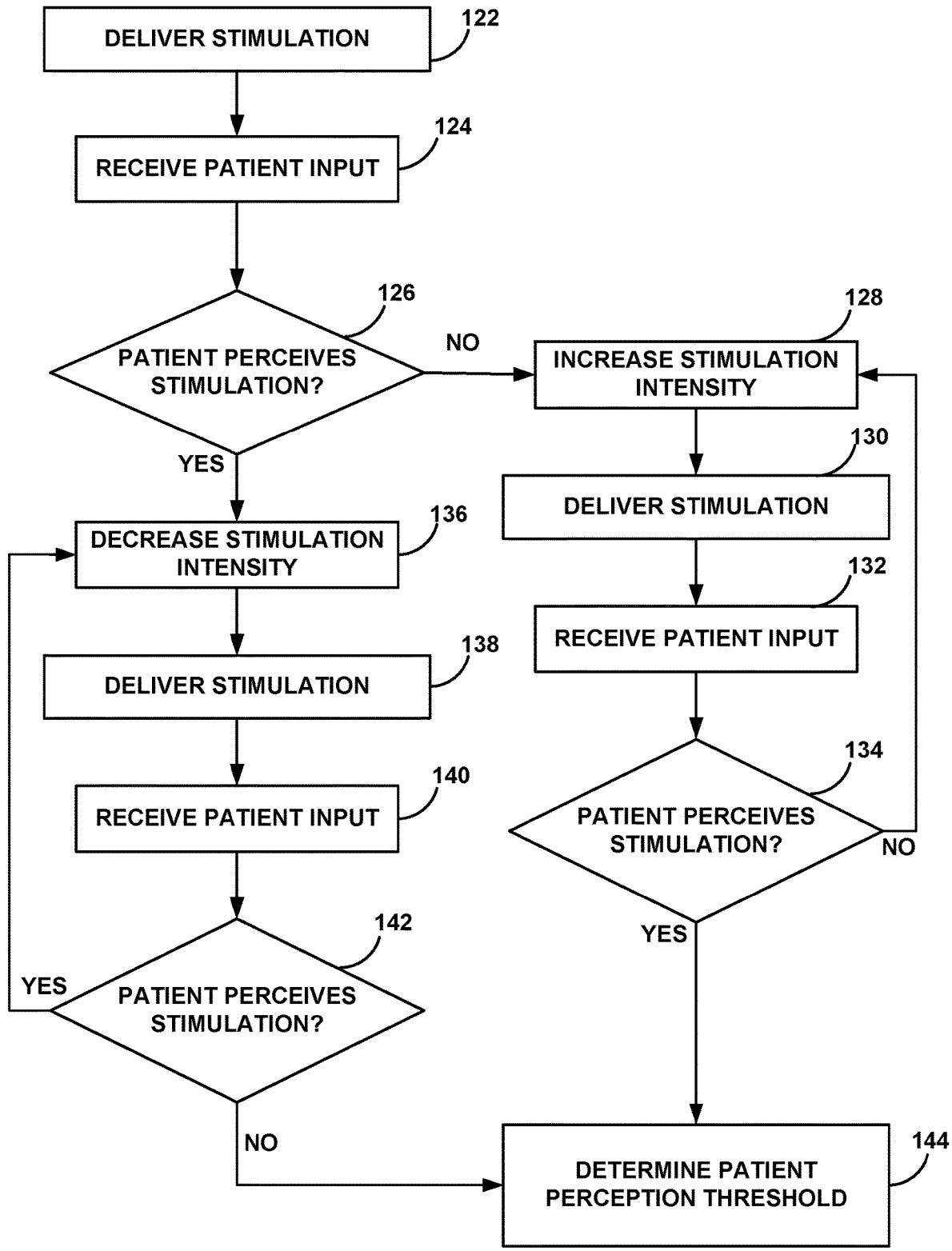
FIG. 7 is a flow diagram illustrating an example technique for determining a patient perception threshold and delivering therapy based on the determination.

FIG. 7 is a flow diagram illustrating an example technique for determining a perception threshold of a patient. As discussed above, in some examples, reminder programs 42 or one or more therapy programs 40 may define electrical stimulation that has an intensity greater than a perception threshold of patient 14, such that patient 14 perceives the electrical stimulation therapy being delivered by IMD 16 according to the respective program. In examples in which patient 14 is to perceive the delivery of electrical stimulation by IMD 16, one or more of components of IMD 16 and programmer 24 may determine a patient perception threshold for the particular patient 14. In some examples, a patient perception threshold may be the lowest intensity of stimulation at which patient 14 perceives the delivery of the electrical stimulation by IMD 16. In other examples, processing circuitry 50 may determine a value for the patient perception threshold based on a typical value. In other examples, however, processing circuitry 50 may determine an individual perception threshold for patient 14 based on actual patient experience.

In the example shown in FIG. 7, processing circuitry 50 controls therapy delivery circuitry 52 to deliver a first trial stimulation pulse to patient 14 at a pre-selected intensity (122). Processing circuitry 50 may receive patient input, e.g., from patient 14 or a patient caretaker provided via user interface 74 of programmer 24 or a similar device, indicating whether patient 14 perceived a physical sensation associated with the first trial stimulation pulse (124). In response to determining the patient input indicates patient 14 perceived the pulse ("YES" branch of block 126), processing circuitry 50 decreases the intensity (e.g., the pulse width or amplitude) of the trial stimulation pulse delivered by therapy delivery circuitry 52 by a predetermined amount (136), and controls therapy delivery circuitry 52 to deliver a second trial stimulation pulse to patient 14 (138). Processing circuitry 50 may receive patient input, e.g., from patient 14 or a patient caretaker, indicating whether patient 14 perceived a physical sensation associated with the second trial stimulation pulse (140). In response to determining the patient input indicates that patient 14 did not perceive the second trial stimulation pulse ("NO" branch of block 142), processing circuitry 50 determines the intensity associated with the first trial stimulation pulse as representing the perception threshold of patient 14 (144). However, if the patient input indicates that patient 14 perceived the second trial stimulation pulse ("YES" branch of block 142), processing circuitry 50 may repeat the part of the technique associated with blocks (128)-(132) until a NO result is obtained ("NO" branch of block 142).

If patient 14 provides input indicating that he or she did not perceive the first trial stimulation pulse ("NO" branch of block 126), then processing circuitry 50 increases the intensity (e.g., the pulse width or amplitude) of the trial stimulation pulse to be delivered by therapy delivery circuitry 52 by a predetermined amount (128), and controls therapy delivery circuitry 52 to deliver a second trial stimulation pulse (130) to patient 14. Processing circuitry 50 may receive patient input indicating whether patient 14 perceived a physical sensation associated with the second trial stimulation pulse (132). If the patient input indicates that patient 14 perceived the second trial stimulation pulse ("YES" branch of block 134), then processing circuitry 50 determines the intensity associated with the second trial stimulation pulse as representing the perception threshold of patient 14 (144). However, the patient input indicates that patient 14 did not perceive the second trial stimulation pulse ("NO" branch of block 134), then processing circuitry 50 may repeat the part of the technique associated with blocks (128)-(132) until a YES result is obtained ("YES" branch of block 134).

Once processing circuitry 50 has determined the perception threshold of patient 14 (144), processing circuitry 50 may store the determined perception threshold in memory 56 of IMD 16 or a memory of another device (e.g., programmer). Processing circuitry 50 may use the stored perception threshold, e.g., to select a therapy program 40 or reminder program 42 from memory 56. For example, processing circuitry 50 may select a reminder program from a plurality of stored reminder programs 42, the selected reminder program having an intensity greater than or equal to the stored perception threshold value. In some examples, the example technique illustrated in FIG. 7 may be repeated more than once the for patient 14, such as at predetermined intervals, or based on patient data stored in memory 56 during the course of treatment.

Figure 8:
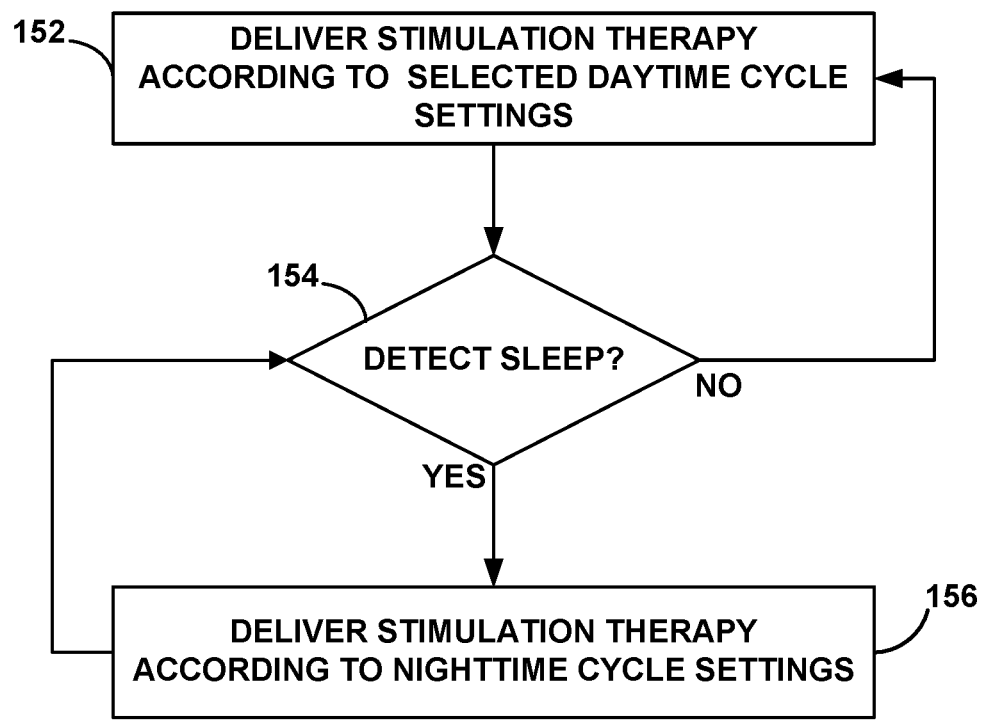
FIG. 8 is a flow diagram illustrating an example technique for determining a sleep status of a patient and delivering therapy based on the determination.

FIG. 8 is a flow diagram illustrating an example technique for controlling delivery of electrical stimulation by IMD 16 based on a determination of whether patient 14 is asleep. As described above with respect to FIG. 5, the values of time X and time Y of a cycle setting may be selected by processing circuitry 50 in such a way so as to take circadian rhythms of patient 14 into account. For example, a value of an urge length (time X in some examples) may vary between times at which a patient is awake, such as day time, and times at which the patient is asleep, such as night time. Thus, in some examples, the time X value of a cycle setting being implemented by IMD 16 may increase or decrease when patient 14 is asleep. Variations in a value of a bladder fill time (time Y in some examples) also may vary depending on whether patient 14 is awake or asleep, and may be caused, for example, by variations in activity of the central nervous system and variations in fluid intake. Thus, in some examples, the time y value of a cycle setting being implemented by IMD 16 may increase or decrease when patient 14 is asleep.

In some examples, a cycle setting may include at least one daytime cycle setting and at least one nighttime cycle setting. In some examples, a nighttime cycle setting may cause IMD 16 to suspend the delivery of electrical stimulation therapy. In addition, the therapy program defining the parameters for the electrical stimulation signal may include a daytime subprogram that defines electrical stimulation at or above a patient perception threshold, and a nighttime subprogram that defines electrical stimulation below the patient perception threshold. For any cycle setting that includes a daytime cycle setting and a nighttime cycle setting, IMD 16 may determine a sleep status of patient 14, i.e., determine whether patient 14 is awake or asleep, and deliver select one of the daytime cycle setting or the nighttime cycle setting accordingly.

In the example shown in FIG. 8, processing circuitry 50 controls therapy delivery circuitry 52 to generate and deliver electrical stimulation therapy to patient 14 according to a daytime cycle setting (152). Processing circuitry 50 may determine a sleep status of patient 14 (154). For example, in examples in which sensing circuitry 22 includes a patient motion sensor that generates a signal indicative of patient activity level or posture state, processing circuitry 50 may determine whether patient 14 is awake or asleep based on signals received from sensing circuitry 22 that indicate a patient activity level and/or a posture state, although other indicators of a waking or sleeping state may be employed. For example, a patient activity level that is less than or equal to a threshold may cause processing circuitry 50 to determine that patient 14 is asleep. As another example, a patient posture state indicative of relatively supine or prone position, alone or in conjunction with a patient activity level that is less than or equal to a threshold, may cause processing circuitry 50 to determine that patient 14 is asleep. In still other examples, processing circuitry 50 may determine a length of time that patient 14 has been at least one of inactive or in a posture state associated with sleep, and may determine that patient 14 is asleep only when patient 14 has been at least one of inactive or in a posture associated with sleep for at least a specified length of time. Other suitable techniques for determining whether patient 14 is asleep, e.g., based on physiological parameters such as respiratory rate and the like, may be used. In some examples, processing circuitry 50 may determine whether patient 14 is asleep (154) at predetermined intervals, such as at intervals of approximately once per hour or at a specific number of times per hour, for example.

In response to determining that patient 14 is asleep ("YES" branch of block 154), processing circuitry 50 may control therapy delivery circuitry 52 to deliver electrical stimulation therapy to patient 14 according to a nighttime cycle setting of the selected cycle setting (156). In response to determining patient 14 is not asleep ("NO" branch of block 154), processing circuitry 50 may control therapy delivery circuitry 52 to deliver electrical stimulation therapy to patient 14 according to a daytime cycle setting of the selected cycle setting (152).

Figure 9:
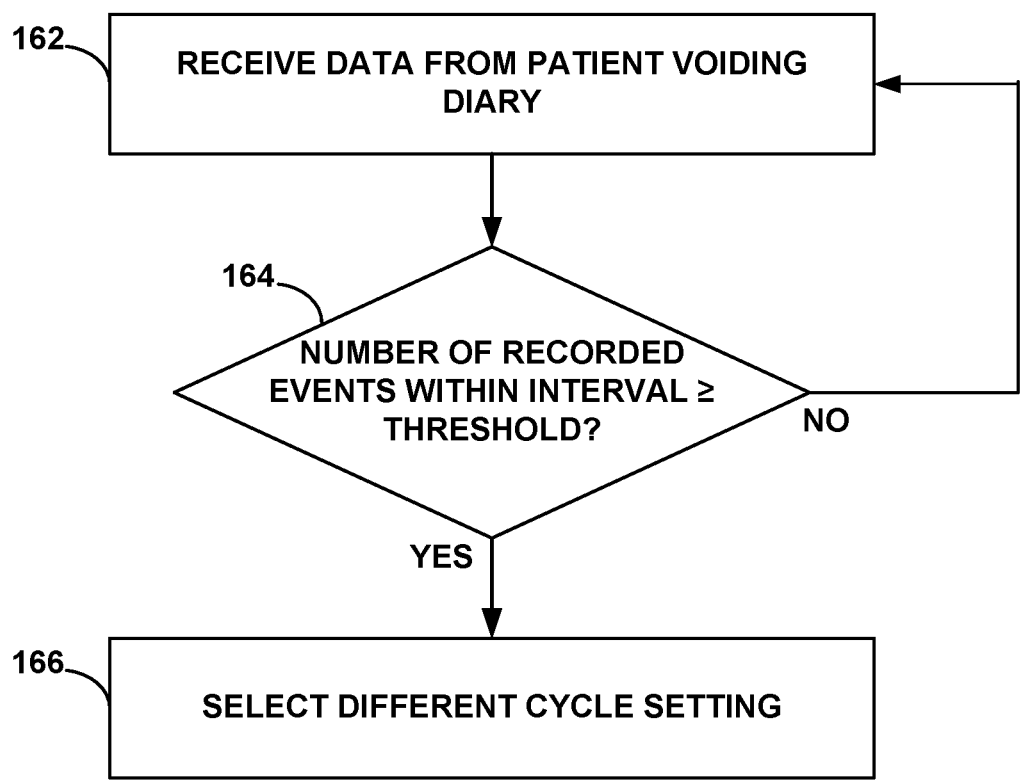
FIG. 9 is a flow diagram illustrating an example technique for selecting one or more cycle settings based on a determination of whether a number of recorded events is equal to or greater than a threshold value.

FIG. 9 is a flow diagram illustrating an example technique by which processing circuitry 50 may determine whether to select a different cycle setting, e.g., at the end of a cycle time period of a currently used cycle setting or during the cycle time period of the currently used cycle setting. In addition to automatically varying the cycle setting at the end of a cycle time period, the example technique according to FIG. 9 may also include varying the cycle settings and/or the cycle time period when a number of recorded symptom-related events within a predetermined interval of time is equal to or greater than a threshold value. Thus, in examples having a predetermined interval time shorter than the selected cycle time period, processing circuitry 50 may select different cycle settings and/or cycle time period before the end of a current cycle time period. In such examples, a recurrence of symptoms or a patient adaptation to the electrical stimulation therapy may be addressed and treated promptly prior to the expiration of a current cycle time period.

In some examples, a voiding diary of a patient stored in memory 56 of IMD 16 may, as discussed above with respect to FIGS. 1 and 2, include data pertaining to the number, timing, and frequency of symptom-related events such as involuntary voiding events (e.g., urine leakage incidents), patient requests for additional electrical stimulation therapy, unwanted sensations or frequency of urgency (as indicated by input from patient 14), and the like. The data pertaining to the number, timing, and frequency of symptom-related events may be received from patient 14, e.g., via user interface 74 of programmer 24, or from a sensor, such as from sensing circuitry 22 or impedance module 54 of IMD 16. In some examples, processing circuitry 50 of IMD 16 may monitor the number of symptom-related events recorded in the voiding diary of patient 14 that occur within a predetermined interval of time, e.g., within one day, one week, or any other appropriate interval, and may select a different cycle setting and/or a different cycle time period upon determining that the number of such events is equal to or greater than a threshold number.

Processing circuitry 50 receives data from the voiding diary of patient 14 (162), such as by retrieving the data from memory 56 or by receiving the data from programmer 24. Processing circuitry 50 determines whether a number of symptom-related events recorded in the voiding diary for a predetermined interval of time is greater than or equal to the threshold number for the predetermined interval of time (164). In response to determining the number of symptom-related events is greater than or equal to the threshold number ("YES" branch of block 164), processing circuitry 50 may select a different cycle setting for controlling delivery of electrical stimulation therapy by IMD 16 (166). The different cycle setting may differ from the first cycle setting, e.g., by at least one of the time X or the time Y. In some examples, processing circuitry 50 may control therapy delivery circuitry 52 to deliver electrical stimulation according to the different cycle setting immediately upon determining that the number of symptom-related events is greater than or equal to the threshold. In other examples, however, processing circuitry 50 may wait until the end of a therapy cycle of the cycle setting, or until the end of the cycle time period to control therapy delivery circuitry 52 to deliver electrical stimulation according to the different cycle setting. Processing circuitry 50 may select the different cycle setting according to a preordered list of cycle settings, according to a randomized or pseudo-randomized pattern as described above with respect to FIG. 5, or based on other criteria, such as past efficacy of the use of particular cycle settings and/or cycle time periods for patient 14.

In response to determining the number of symptom-related events is less than the threshold for the predetermined interval of time ("NO" branch of block 164), then processing circuitry 50 may continue reviewing the data from the voiding diary (162).

FIG. 10 is a flow diagram illustrating an example technique for delivering reminder electrical stimulation to patient 14. According to the example technique of FIG. 10, IMD 16 may deliver reminder stimulation to patient 14 according to a reminder program selected from memory 56 by processing circuitry 50 (112). A reminder program may include electrical stimulation parameter values by which IMD 16 delivers reminder stimulation, which may be electrical stimulation above a perception threshold of patient 14. The reminder electrical stimulation may remind patient 14 of the presence of IMD 16, the availability of electrical stimulation therapy, and/or the condition of patient 14, such that patient 14 is more aware of the need to voluntarily void or to take other measures to control the incontinence condition of patient 14. In some examples, the reminder stimulation evokes a physiological response from patient 14 that provides a therapeutic result (e.g., a sphincter contraction or reduction in bladder contraction frequency). In other examples, however, the reminder stimulation does not evoke a physiological response from patient 14 that provides a therapeutic result, but, rather, merely serves as a reminder to patient 14 of the presence of IMD 16, the availability of electrical stimulation therapy, and/or the condition of patient 14.

In some examples, a reminder program 42 may define electrical stimulation parameter values by which IMD 16 delivers reminder stimulation when processing circuitry 50 determines that patient 14 is awake, referred to herein as a "daytime sub-program" of a reminder program. In addition, in some of these examples, a reminder program may also include parameters values by which IMD 16 delivers reminder stimulation when processing circuitry 50 determines that patient 14 is asleep, referred to herein as a "nighttime sub-program" of a reminder program.

In one example, IMD 16 may deliver reminder stimulation only when processing circuitry 50 determines that patient 14 is awake. However, in another example, IMD 16 also may deliver reminder stimulation when processing circuitry 50 determines that patient 14 is asleep, according to a nighttime sub-program of the selected reminder program. For example, a nighttime sub-program of the selected reminder program may cause IMD 16 to deliver reminder stimulation to patient 14 according to a different intensity and/or a different schedule than a daytime sub-program of the same reminder program. In some examples, a nighttime sub-program of a reminder program may cause IMD 16 to deliver reminder stimulation that has a lower or higher intensity when patient 14 is asleep than the reminder stimulation that IMD 16 delivers according to a daytime subset of the same reminder program. In such examples, a nighttime sub-program also may cause IMD 16 to deliver reminder stimulation more or less frequently when patient 14 is asleep than the reminder stimulation that IMD delivers according to a daytime sub-program of the same reminder program. Thus, for some selected reminder programs, processing circuitry 50 may determine whether patient 14 is awake or asleep and cause IMD 16 to deliver reminder stimulation accordingly.

In the example shown in FIG. 10, processing circuitry 50 causes therapy delivery circuitry 52 to generate and deliver reminder stimulation to patient 14 according to a daytime sub-program of the selected reminder program for delivering reminder therapy (172). Processing circuitry 50 determines whether patient 14 is awake or asleep (154), e.g., using the techniques described above with respect to FIG. 8. In some examples, processing circuitry 50 may make the determination of whether patient 14 is asleep (154) at predetermined intervals, such as at intervals of approximately once per hour, or at a specific number of times per hour.

In response to determining that patient 14 is asleep ("YES" branch of block 154), processing circuitry 50 controls therapy delivery circuitry 52 to deliver reminder stimulation to patient 14 according to a nighttime sub-program of the selected reminder program at (176). In some examples, no reminder electrical stimulation is delivered to patient 14 when the nighttime sub-program is implemented. In response to determining that patient 14 is awake ("NO" branch of block 154), processing circuitry 50 controls therapy delivery circuitry 52 to deliver reminder stimulation to patient 14 according to a daytime sub-program of the selected reminder program at (172).

Figure 11:
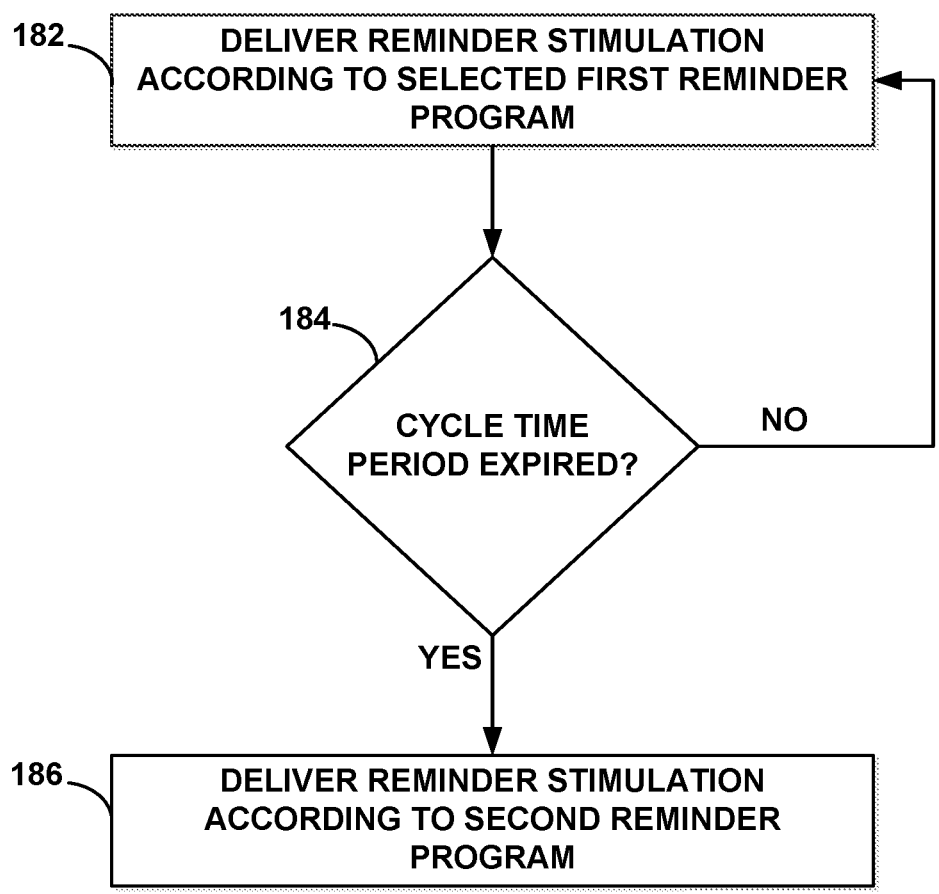
FIG. 11 is a flow diagram illustrating another example technique for delivering reminder therapy to a patient based on a cycle time period.

FIG. 11 is a flow diagram illustrating an example technique by which processing circuitry may control IMD 16 to deliver reminder stimulation according to a plurality of cycle settings. Patient 14 may become accustomed to an electrical stimulation, including reminder stimulation, which may result in a reduced effect of the electrical stimulation delivered by IMD 16 on patient 14 over time. In accordance with the technique shown in FIG. 11, the occurrence of patient adaptation to the reminder stimulation may be reduced by varying one or more parameter values of the reminder stimulation, such that reminder stimulation is not delivered to patient 14 according to the same parameter values for a relatively long period of time. Delivering reminder stimulation to patient 14 according to a combination of different reminder programs over the course of one or more cycle time periods may help minimize patient adaptation to the reminder stimulation.

In the example shown in FIG. 11, processing circuitry 50 may control therapy delivery circuitry 52 to deliver reminder electrical stimulation to patient 14 according to a first reminder program (182). The first reminder program may define stimulation parameter values such as the amplitude, frequency, pulse width, and duty cycle by which the reminder stimulation is to be delivered. Processing circuitry 50 may determine whether a current cycle time period has expired (184). The cycle time period may be, for example, associated with a currently implemented cycle setting, or may be associated with the first reminder program. In response to determining that the current cycle time period has expired ("YES" branch of block 184), processing circuitry 50 controls therapy delivery circuitry 52 to stop delivering reminder stimulation to patient 14 according to the first reminder program, and to deliver reminder stimulation to patient 14 according to a second reminder program (186). The second reminder program may define at least one different stimulation parameter value from the first reminder program. In response to determining that the current cycle time period has not expired ("NO" branch of block 184), processing circuitry 50 may control therapy delivery circuitry 52 to continue delivering reminder stimulation to patient 14 according to the first reminder program at (182).

Processing circuitry 52 may determine the second reminder program using any suitable technique. For example, memory 56 may store a list of a plurality of reminder programs 42 (FIG. 3), and processing circuitry 50 may psuedorandomly select a reminder program from the list, e.g., using a pseudo random counter, each number in the counter being associated with a stored reminder program. As another example, memory 56 may store a list of a plurality of reminder programs 42 in a predetermined order, and processing circuitry 50 may select a reminder program from the list in the predetermined order.

While the techniques described above are primarily described as being performed by processing circuitry 50 of IMD 16 or processing circuitry 70 of programmer 24, in other examples, one or more other processors may perform any part of the techniques described herein alone or in addition to processing circuitry 50 or processing circuitry 70. Thus, reference to "processing circuitry" may refer to "one or more processing circuitries." Likewise, "one or more processing circuitries" may refer to single or multiple processing circuitries in different examples.

For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein. The parameters associated with the cycle settings described above may be stored in memory of the IMD or in memory of another device, and used by processing circuitry 50 to control delivery of the electrical stimulation.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various aspects of the disclosure have been described. These and other aspects are within the scope of the following claims.

What is claimed is:

1. A method comprising:
  determining, by processing circuitry, a first cycle time period;
  controlling, by the processing circuitry, a medical device to deliver continuous electrical stimulation therapy to a patient over the first cycle time period;
  determining, by the processing circuitry, a cycle setting for electrical stimulation therapy, wherein the cycle setting defines an on-cycle of about 30 minutes and an off-cycle of at least about 23.5 hours;
  determining, by the processing circuitry, a second cycle time period of about at least 28 days; and
  controlling, by the processing circuitry, the medical device to deliver the electrical stimulation therapy to the patient according to the cycle setting over the second cycle time period.

2. The method of claim 1, wherein the first cycle time period and the second cycle time period are equal.

3. The method of claim 1, wherein the first cycle time period and the second cycle time period are different.

4. The method of claim 1, wherein the on-cycle is selected to evoke a physiological response of the patient.

5. The method of claim 4, wherein the physiological response comprises a urinary sphincter contraction or a reduction in bladder contraction frequency.

6. The method of claim 1, wherein the electrical stimulation therapy is at or above a perception threshold of the patient.

7. The method of claim 1, wherein the electrical stimulation therapy is below a perception threshold of the patient.

8. The method of claim 1, wherein the first cycle time period is on the order of days.

9. The method of claim 1, wherein determining the cycle setting comprises determining the cycle setting based on one or more corresponding power consumption values.

10. The method of claim 1, wherein determining, by the processing circuitry, the cycle setting comprises selecting a next cycle setting in an ordered list of cycle settings.

11. The method of claim 1, wherein the second cycle time period follows the first cycle time period, and does not overlap with the first cycle time period.

12. The method of claim 1, further comprising:
determining, by the processing circuitry, a third cycle setting for the electrical stimulation therapy; and
controlling, by the processing circuitry, the medical device to deliver the electrical stimulation therapy to the patient according to the third cycle setting prior to an end of the second cycle time period.

13. The method of claim 12, further comprising:
determining, by the processing circuitry, a number of symptom-related events of the patient for a predetermined interval of time,
wherein determining the third cycle setting comprises determining the third cycle setting in response to determining the number of symptom-related events for the predetermined interval of time is greater than or equal to a threshold value.

14. The method of claim 1, further comprising:
determining, by the processing circuitry, that the medical device is to deliver the continuous electrical stimulation therapy to the patient for an additional first cycle time period;
controlling, by the processing circuitry, the medical device to deliver the continuous electrical stimulation therapy to the patient for the additional first cycle time period after delivery of the continuous electrical stimulation therapy over the first cycle time period; and
after delivery of the continuous electrical stimulation therapy for the additional first cycle time period, determining, by the processing circuitry, that the medical device is to not deliver the continuous electrical stimulation therapy to the patient for another first cycle time period,
wherein controlling, by the processing circuitry, the medical device to deliver the electrical stimulation therapy to the patient according to the cycle setting over the second cycle time period comprises controlling, by the processing circuitry, the medical device to deliver the electrical stimulation therapy to the patient according to the cycle setting over the second cycle time period, in response to determining that the medical device is to not deliver the continuous electrical stimulation therapy to the patient.

15. The method of claim 1, wherein the cycle setting comprises a first cycle setting, the on-cycle comprises a first on-cycle, and the off-cycle comprises a first off-cycle, the method further comprising:

determining an additional cycle setting for the electrical stimulation therapy that defines an additional on-cycle and an additional off-cycle for the electrical stimulation therapy, wherein an amount of time for the additional on-cycle and the additional off-cycle is approximately the same; and
controlling the medical device to deliver the electrical stimulation therapy to the patient according to the additional cycle setting subsequent to delivery of the continuous electrical stimulation therapy and prior to delivery of the electrical stimulation therapy to the patient according to the cycle setting.

16. The method of claim 1, wherein controlling the medical device to deliver the continuous electrical stimulation therapy comprises controlling the medical device to deliver the continuous electrical stimulation therapy to at least one of a sacral nerve or a tibial nerve of the patient, and wherein controlling the medical device to deliver the electrical stimulation therapy to the patient according to the cycle setting comprises controlling the medical device to deliver the electrical stimulation therapy to at least one of the sacral nerve or tibial nerve of the patient according to the cycle setting.

17. A system comprising:
therapy delivery circuitry configured to generate and deliver electrical stimulation therapy to a patient; and
processing circuitry configured to:
determine a first cycle time period,
control the therapy delivery circuitry to deliver continuous electrical stimulation therapy to the patient over the first cycle time period,
determine a cycle setting for the electrical stimulation therapy, wherein the cycle setting defines an on-cycle of about 30 minutes and an off-cycle of at least about 23.5 hours,
determine a second cycle time period of about at least 28 days, and
control the therapy delivery circuitry to deliver the electrical stimulation therapy to the patient according to the cycle setting over the second cycle time period.

18. The system of claim 17, wherein the first cycle time period and the second cycle time period are equal.

19. The system of claim 17, wherein the first cycle time period and the second cycle time period are different.

20. The system of claim 17, wherein the on-cycle is selected to evoke a physiological response of the patient.

21. The system of claim 20, wherein the physiological response comprises a urinary sphincter contraction or a reduction in bladder contraction frequency.

22. The system of claim 17, wherein the electrical stimulation therapy is at or above a perception threshold of the patient.

23. The system of claim 17, wherein the electrical stimulation therapy is below a perception threshold of the patient.

24. The system of claim 17, wherein the first cycle time period is on the order of days.

25. The system of claim 17, wherein the processing circuitry is configured to determine the cycle setting based on one or more corresponding power consumption values.

26. The system of claim 17, further comprising a memory storing an ordered list of a plurality of cycle settings, wherein the processing circuitry is configured to determine the cycle setting by at least selecting a next cycle setting in the ordered list of cycle settings.

27. The system of claim 17, wherein the second cycle time period follows the first cycle time period, and does not overlap with the first cycle time period.

28. The system of claim 17, wherein the processing circuitry is further configured to:
determine a third cycle setting for the electrical stimulation therapy, and
control the therapy delivery circuitry to deliver the electrical stimulation therapy to the patient according to the third cycle setting prior to an end of the second cycle time period.

29. The system of claim 28, further comprising a memory that stores indications of symptom-related events of the patient, wherein the processing circuitry is further configured to determine a number of symptom-related events of the patient for a predetermined interval of time, and wherein the processing circuitry is configured to determine the third cycle setting in response to determining the number of symptom-related events for the predetermined interval of time is greater than or equal to a threshold value.

30. The system of claim 17, wherein the processing circuitry is configured to:
determine that the therapy delivery circuitry is to deliver the continuous electrical stimulation therapy to the patient for an additional first cycle time period;
control the therapy delivery circuitry to deliver the continuous electrical stimulation therapy to the patient for the additional first cycle time period after delivery of the continuous electrical stimulation therapy over the first cycle time period; and
after delivery of the continuous electrical stimulation therapy for the additional first cycle time period, determine that the therapy delivery circuitry is to not deliver the continuous electrical stimulation therapy to the patient for another first cycle period,
wherein the processing circuitry is configured to control the therapy delivery circuitry to deliver the electrical stimulation therapy to the patient according to the cycle setting over the second cycle time period, in response to determining that the medical device is to not deliver the continuous electrical stimulation therapy to the patient.

31. The system of claim 17, wherein the cycle setting comprises a first cycle setting, the on-cycle comprises a first on-cycle, and the off-cycle comprises a first off-cycle, and wherein the processing circuitry is configured to:
determine an additional cycle setting for the electrical stimulation therapy that defines an additional on-cycle and an additional off-cycle for the electrical stimulation therapy, wherein an amount of time for the additional on-cycle and the additional off-cycle is approximately the same; and
control the therapy delivery circuitry to deliver the electrical stimulation therapy to the patient according to the additional cycle setting subsequent to delivery of the continuous electrical stimulation therapy and prior to delivery of the electrical stimulation therapy to the patient according to the cycle setting.

32. The system of claim 17, wherein to control the therapy delivery circuitry to deliver the continuous electrical stimulation therapy, the processing circuitry is configured to control the therapy delivery circuitry to deliver the continuous electrical stimulation therapy to at least one of a sacral nerve or a tibial nerve of the patient, and wherein to control the therapy delivery circuitry to deliver the electrical stimulation therapy to the patient according to the cycle setting, the processing circuitry is configured to control the therapy delivery circuitry to deliver the electrical stimulation therapy to at least one of the sacral nerve or tibial nerve of the patient according to the cycle setting.

33. A system comprising:
means for generating and delivering electrical stimulation to a patient;
means for determining a first cycle time period;
means for controlling the means for generating and delivering electrical stimulation to deliver continuous electrical stimulation therapy to a tibial nerve of the patient over the first cycle time period;
means for determining a cycle setting for electrical stimulation therapy, wherein the cycle setting defines an on-cycle of about 30 minutes and an off-cycle of at least about 23.5 hours;
means for determining a second cycle time period of about at least 28 days; and
means for controlling the means for generating and deliver electrical stimulation to deliver the electrical stimulation therapy to the patient according to the cycle setting to the tibial neve of the patient over the second cycle time period.

34. The system of claim 33, wherein the means for determining the cycle setting comprises means for selecting a next cycle setting in an ordered list of cycle settings.

35. A non-transitory computer-readable storage medium comprising instructions that, when executed by processing circuitry, cause the processing circuitry to:
determine a first cycle time period;
control a medical device to deliver continuous electrical stimulation therapy to a patient over the first cycle time period;
determine a cycle setting for electrical stimulation therapy, wherein the cycle setting defines an on-cycle of about 30 minutes and an off-cycle of at least about 23.5 hours;
determine a second cycle time period of about at least 28 days; and
control the medical device to deliver the electrical stimulation therapy to the patient according to the cycle setting over the second cycle time period.

36. A method comprising:
determining, by processing circuitry, a first cycle setting for electrical stimulation therapy, wherein the first cycle setting defines a first on-cycle and a first off-cycle for the electrical stimulation therapy;
determining, by the processing circuitry, a first cycle time period;
controlling, by the processing circuitry, a medical device to deliver the electrical stimulation therapy to a patient according to the first cycle setting over the first cycle time period;
determining, by the processing circuitry, that the medical device is to deliver the electrical stimulation therapy to the patient for an additional first cycle time period according to the first cycle setting;
controlling, by the processing circuitry, the medical device to deliver the electrical stimulation therapy to the patient for the additional first cycle time period according to the first cycle setting immediately after delivery of the electrical stimulation therapy according to the first cycle setting over the first cycle time period; and
after delivery of the electrical stimulation therapy for the additional first cycle time period, determining, by the processing circuitry, that the medical device is to not deliver the electrical stimulation therapy to the patient according to the first cycle setting;

determining, by the processing circuitry, a second cycle setting for the electrical stimulation therapy, wherein the second cycle setting defines a second on-cycle and a second off-cycle, wherein the second cycle setting is different from the first cycle setting;

determining, by the processing circuitry, a second cycle time period; and controlling, by the processing circuitry, the medical device to deliver the electrical stimulation therapy to the patient according to the second cycle setting over the second cycle time period, in response to determining that the medical device is to not deliver the electrical stimulation therapy to the patient according to the first cycle setting.

37. A system comprising:

therapy delivery circuitry configured to generate and deliver electrical stimulation therapy to a patient; and processing circuitry configured to:
 determine a first cycle setting for electrical stimulation therapy, wherein the first cycle setting defines a first on-cycle and a first off-cycle for the electrical stimulation therapy;
 determine a first cycle time period;
 control the therapy delivery circuitry to deliver the electrical stimulation therapy to the patient according to the first cycle setting over the first cycle time period;
 determine that the therapy delivery circuitry is to deliver the electrical stimulation therapy to the patient for an additional first cycle time period according to the first cycle setting;
 control the therapy delivery circuitry to deliver the electrical stimulation therapy to the patient for the additional first cycle time period according to the first cycle setting immediately after delivery of the electrical stimulation therapy according to the first cycle setting over the first cycle time period; and
 after delivery of the electrical stimulation therapy for the additional first cycle time period, determine that the therapy delivery circuitry is to not deliver the electrical stimulation therapy to the patient according to the first cycle setting;
 determine a second cycle setting for the electrical stimulation therapy, wherein the second cycle setting defines a second on-cycle and a second off-cycle, wherein the second cycle setting is different from the first cycle setting;
 determine a second cycle time period; and
 control the therapy delivery circuitry to deliver the electrical stimulation therapy to the patient according to the second cycle setting over the second cycle time period, in response to determining that the therapy delivery circuitry is to not deliver the electrical stimulation therapy to the patient according to the first cycle setting.

* * * * *